US007709189B1

(12) United States Patent
Cohen

(10) Patent No.: US 7,709,189 B1
(45) Date of Patent: May 4, 2010

(54) METHODS FOR IDENTIFYING OR DIAGNOSING CARCINOMA CELLS WITH METASTATIC POTENTIAL BASED ON THE MEASUREMENT OF LYMPHOID GENES OR THEIR PRODUCTS IN CARCINOMA CELLS

(76) Inventor: Stefan A. Cohen, 24 Wagon Wheel Dr., East Amherst, NY (US) 14051

( * ) Notice: Subject to any disclaimer, the term of this patent is extended or adjusted under 35 U.S.C. 154(b) by 74 days.

(21) Appl. No.: 12/218,586

(22) Filed: Jul. 16, 2008

Related U.S. Application Data

(60) Continuation of application No. 10/939,764, filed on Sep. 13, 2004, now abandoned, which is a division of application No. 09/110,376, filed on May 12, 1998, now Pat. No. 6,790,604.

(51) Int. Cl.
*C12Q 1/00* (2006.01)
*C12Q 1/68* (2006.01)
*G01N 33/53* (2006.01)

(52) U.S. Cl. .................................. 435/4; 435/6; 435/7.1; 436/64

(58) Field of Classification Search ........................ None
See application file for complete search history.

(56) References Cited

U.S. PATENT DOCUMENTS

| 4,690,915 | A | 9/1987 | Rosenberg |
| 4,789,658 | A | 12/1988 | Yoshimoto et al. |
| 4,939,093 | A | 7/1990 | McGrogan et al. |
| 5,006,459 | A | 4/1991 | Kung et al. |
| 5,061,488 | A | 10/1991 | Wiltrout et al. |
| 5,089,261 | A | 2/1992 | Nitecki et al. |
| 5,098,702 | A | 3/1992 | Zimmerman et al. |
| 5,126,129 | A | 6/1992 | Wiltrout et al. |
| 5,229,109 | A | 7/1993 | Grimm et al. |
| 5,536,642 | A | 7/1996 | Barbera-Guillem et al. |
| 6,790,604 | B1 | 9/2004 | Cohen et al. |

FOREIGN PATENT DOCUMENTS

WO       WO95/07462       3/1995

OTHER PUBLICATIONS

Latour et al (Journal of Biological Chemistry, 1998, vol. 17, pp. 2584-2595).*
R. Tsunoda et al, "Emperipolesis of Lymphoid Cells by Human Follicular Dendritic Cells in Vitro," *Virchows Archiv. B Cell Pathol.*, 1992, 62:69-78.
A. Weissman et al, "Role of the Zeta Chain in the Expression of the T Cell Antigen Receptor: Genetic Reconstitution Studies," *The EMBO Journal*, 1989, 8(12): 3651-3656.
U, Kim, "Pathogenesis and Characteristics of Spontaneously Metastasizing Mammary Carcinomas and The General Principle of Metastasis," *J. of Surgical Oncology*, 1986, 33: 151-165.
H. O'Neill et al, "Germline Transcription and Expression of Tcrb-V8 Genes in Peripheral Mouse Lymphoid Tissues," *Immunogenesis*, 1995, 42: 309-314.

G. Basi et al, "Antibodies to Soluble Human T Cell Receptor B Chain Recognize Multiple Epitopes on Cell Surface TCR," *Journal of Immunological Methods*, 1992, 155: 175-191.
D. Center et al, "Interleukin 16 and its Function as a CD4 Ligand," *Immunology Today*, 1996, 17(10): 476-481.
S. McCracken et al, "An Alternative Pathway for Expression of p56$^{lck}$ From Type I Promoter Transcripts in Colon Carcinoma," *Oncogene*, 1997, 15: 2929-2937.
I. Fidler, "Critical Factors in the Biology of Human Cancer Metastasis: Twenty-eighth G.H.A. Clowes Memorial Award Lecture," *Cancer Research*, 1990, 50: 6130-6138.
M. Davis, "T Cell Receptor Gene Diversity and Selection," *Annual Review of Biochemistry*, 1990, 59: 475-496.
U. Latza et al, "Ber-EP4: New Monoclonal Antibody Which Distinguishes Epithelia From Mesothelia," *J. Clin. Pathol.*, 1990, 43: 213-219.
J. Pugin et al, "Lipopolysaccharide Activation of Human Endothelial and Epithelial Cells is Mediated by Lipopolysaccharide-binding Protein and Soluble CD14," *Proc. Natl. Acad. Sci. USA*, 1993, 90: 2744-2748.
C. Bleul et al, "The HIV Coreceptors CXCR4 and CCR5 Are Differentially Expressed and Regulated on Human T Lymphocytes," *Proc. Natl. Acad. Sci. USA*, 1997, 94: 1925-1930.
E. Ruoslanti, "How Cancer Spreads," *Scientific American*, Sep. 1996, 72-77.
U. Kim et al, "Immunological Escape Mechanism in Spontaneously Metastasizing Mammary Tumors," *Proc. Nat. Acad. Sci. USA*, 1975, 72(3): 1012-1016.
S. Cohen et al, "Capacity of Nonparenchymal Liver Cells to Control Metastasis," *NK Cells in the Liver*, R.G. Landes Company, Austin, 1995, 71-100.
T. Springer, "Traffic Signals for Lymphocyte Recirculation and Leukocyte Emigration: The Multistep Paradigm," *Cell*, 1994, 76: 301-314.
S. Latour et al, "Differential Intrinsic Enzymatic Activity of Syk and Zap-70 Protein-Tyrosine Kinases," *The Journal of Biological Chemistry*, 1996, 271(37):22782-22790.
S. Candeias ,et al, "T Cell Receptor VB 8.2 Gene Germ-line Transcription: An Early Event of Lymphocyte Differentiation," *Eur. J. Immunol.*, 1994, 24: 3073-3081.
E. Yefenof et al, "Cancer Dormancy: Isolation and Characterization of Dormant Lymphoma Cells," *Proc. Natl. Acad. Sci. USA*, 1993, 90: 1829-1833.
S. Lee et al, "Ly-6A is Required for T Cell Receptor Expression and Protein Kinase Fyn Activity," *The EMBO Journal*, 1994, 13(9): 2167-2176.

(Continued)

*Primary Examiner*—Karen A Canella
(74) *Attorney, Agent, or Firm*—James C. Simmons

(57) ABSTRACT

A method of predicting the lymphotrophic metastatic potential of a solid non-lymphoid tumor. The percentage of cells of each of a plurality of representative samples of the tumor which express lymphoid gene products is determined. The metastatic potential is predicted to be low when no tumor cells in all of the samples are detected to express lymphoid gene products. The metastatic potential is predicted to be high when a high percentage of tumor cells in at least one of the samples are detected to express lymphoid gene products. Expression of SYKB in any of a plurality of samples of a primary colon tumor is indicative that the primary colon tumor has lymphotrophic metastatic potential.

1 Claim, 25 Drawing Sheets

OTHER PUBLICATIONS

M. Omary et al, "HIV-I Infection and Expression in Human Colonic Cells: Infection and Expression in CD4+ and CD4− Cell Lines," *AIDS*, 1991, 5(3)275-281.

U. Kim et al, "Selective Suppression of T Cell Function in Normal Rats Simulating the T-Independent Antitumor and Antimetastatic Reaction of Nude Mice Against Metastasizing Rat Mammary Carcinomas," Immune-Deficient Animals 4th Int. Work-shop on Immune-Deficient Animals in Exp. Res., Chexbres, 1982, 235-238.

K. Mayer et al, "An Essential cis-acting Element of the lck 3' Promoter Regulates the Expression of $56^{lck}$ in Metastatic Colorectal Cancer Cells," *Intl. J. Oncology*, 1993, 3:369-373.

M. Omary et al, "Biochemical and Morphological Differentiation of the Human Colonic Cells Line 5W620 in the Presence of Dimethylsulfoxide," *J. Cellular Biochemistry*, 1992, 48:316-323.

S. Cohen et al, "Role of Asialo-GMI Positive Liver Cells from Athymic Nude or Polyinosinic-Polycytidylic Acid-Treated Mice in Suppressing Colon-derived Experimental Hepatic Metastasis," *Cancer Res.*, 1990, 50:1834-1840.

C. Mallick et al, "Rearrangement and Diversity of T Cell Receptor B Chain Genes in Thymocytes: A Critical Role for the B Chain in Development," *Cell*, 1993, 73: 513-519.

F. Vidal-Vanaclocha et al, "Role of Periportal and Perivenous Sinusoidal Endothelial Cells in Hepatic Homing of Blood and Metastatic Cancer Cells," *Seminars in Liver Disease*, 1993, 13:60-71.

M. Cohn et al, "The Differentiation Antigen Ly-6E.I is Expressed in Mouse Metastatic Tumor Cells Lines," *FEBS Letters*, 1997, 403: 181-185.

J. Viney et al, "Generation of Monoclonal Antibodies Against a Human T Cell Receptor B Chain Expressed in Transgenic Mice," *Hybridoma*, 1992, 11: 701-713.

N. Tomita et al, "Isolation and Characterization of a Highly Malignant Variant of the 5W480 Human Colon Cancer Cell Line," *Cancer Research*, 1992, 52: 6840-6847.

M. O'Reilly, "Angiostatin Induces and Sustains Dormancy of Human Primary Tumors in Mice," *Nature Medicine*, 1996, 2(6): 689-692.

M. Dohlsten et al, "Human Major Histocompatibility Complex Class II—negative Colon Carcinoma Cells Present Staphylococcal Superantigens to Cytotoxic T-lymphocytes: Evidence for a Novel Enterotoxin Receptor," *Eur. J. Immunol.*, 1991, 21:1229-1233.

J. Lamphear, "Intercellular Adhesion Molecule-I and Leukocyte Function-associated Antigen-3 Provide Superantigen-induced T Lymphocyte Proliferation in the Absence of a Specific Presenting Molecule," *The Journal of Immunology*, 1998, 160: 615-623.

O. Kanagawa, "In Vivo T Cell Tumor Therapy With Monoclonal Antibody Directed to the Vβ Chain of T Cell Antigen Receptor," *J. Exp. Med.*, 1989, 170: 1513-1519.

R. Muise-Helmericks et al, "Identification of a Novel Repressive Element in the Proximal lck Promoter," *The Journal of Biological Chemistry*, 1995, 270(46): 27538-27543.

C. Ng et al, "Application of a T Cell Receptor Antibody BF1 for Immunophenotypic Analysis of Malignant Lymphomas," *American Journal of Pathology*, 1988, 132(2): 365-371.

I. Fidler et al, "Metastasis Results from Preexisting Variant Cells Within a Malignant Tumor," *Science*, 1977, 197: 893-895.

N. Wang et al, "Characterization of High- and Low-Metastatic Clones Derived from a Methylcholanthrene-induced Murine Pibrosarcoma," *Cancer Research*, 1982, 42:1046-1051.

F. Sanger, DNA Sequencing With Chain-Terminating Inhibitors, *Proc. Natl. Acad. Sci. USA*, 1977, 74(12) : 5463-5467.

S. Ghosh, "A Tumor-associated Organ-specific Antigen Characteristic of Spontaneously Metastatic Rat Mammary Carcinomas," *JNCI*, 1979, 62(5): 1229-1233.

Barberá-Guillem et al, "Selective Implantation and Growth in Rats and Mice of Experimental Liver Metastasis in Aćinar Zone One," *Cancer Research*, 1989, 49:4003-4010.

S. Yasamura et al, *Proc. Annu. Meet. Am. Assoc. Cancer Res.*, 1992, 33: A 290.

U. Kim et al, "Conversion of MMTV-Induced Mouse Mammary Tumor and EJ-ras Transformed N1H3T3 Sarcoma Cell Lines into Highly Metastasizing Tumors by Fusion With Lymphoid Cells," Abstract 373, *Proceedings of The American Association for Cancer Research*, 1993, 34: 63.

S. Rosenberg et al, "Special Report—Observations on the Systemic Administration of Autoloqous Lymphokine-activated Killer Cells and Recombinant Interleukin-2 to Patients With Metastatic Cancer," *The New England Journal of Medicine*, 1985, 313(23): 1485-1492.

Barberá-Guillem et al, "Differences in the Lectin-binding Patterns of the Periportal and Perivenous Endothelial Domains in the Liver Sinusoids," *Journal of Hepatology*, 1991, 14:131-139.

E. Blum et al, "Non-peptide ITAM Mimics as ZAP-70 Antagonists," *Bioorganic & Medicinal Chemistry Letters*, 1997, 7(22): 2875-2878.

Kim et al, "Manifestation of Lymphotropic Metastatic Potential and Expression of Deoxynucleotidyl Terminal Transferase Activities . . . ," *Proceedings of the American Assn. for Cancer Research*, 1988.

Paul, *Fundamental Immunology*, 3rd ed., p. 976-977, 1993.

Grignon et al,"Cross-Reactivity to a Monoclonal Pan T-cell Antibody with Prostate Epithelium," *J. Urology*, 137: 330-332, 1987.

Revesz et al, *Bioorganic and Medicinal Chemistry Letters*, 1997, vol. 7, pp. 2875-2878.

Jones et al, *Advanced Drug Delivery Reviews*, 1998, pp. 153-170.

*Stedman's Medical Dictionary*, 27$^{th}$ Edition, 2000.

\* cited by examiner

A

```
    1          11         21         31         41         51         61         71
TGCACAGTGGGGTCAGCACAGACCCGCAGCCCCTCAAGGAGCAGCCCGCCCTCAATGACTCCAGATACTGCCTGAGCAGC......PBL
TGCACAGTGGGGTCAGCACAGACCCGCAGCCCCTCAAGGAGCAGCCCGCCCTCAATGACTCCAGATACTGCCTGAGCAGC......SW480
TGCACAGTGGGGTCAGCACAGACCCGCAGCCCCTCAAGGAGCAGCCCGCCCTCAATGACTCCAGATACTGCCTGAGCAGC......SW620

81         91        101        111        121        131        141        151        161
CGCCTGAGGGTCTCGGCCACCTTCTGCAGAGAACCCCGCAACCACTTCCGCTGTCAAGTCAGTTCTACGGGCTCTCGGAG
CGCCTGAGGGTCTCGGCCACCTTCTGCAGAGAACCCCGCAACCACTTCCGCTGTCAAGTCAGTTCTACGGGCTCTCGGAG
CGCCTGAGGGTCTCGGCCACCTTCTGCAGAGAACCCCGCAACCACTTCCGCTGTCAAGTCAGTTCTACGGGCTCTCGGAG 171        181        191        201        211        221        231        241
AATGACGAGTGGACCCAGGATAGGGCCAAACCCGTCACCCAGATCGTCAGCGCCGAGGCCTGGGGTAGAGCAGACTGTGG
AATGACGAGTGGACCCAGGATAGGGCCAAACCCGTCACCCAGATCGTCAGCGCCGAGGCCTGGGGTAGAGCAGACTGTGG
AATGACGAGTGGACCCAGGATAGGGCCAAACCCGTCACCCAGATCGTCAGCGCCGAGGCCTGGGGTAGAGCAGACTGTGG 251        261
CTTTACCTCGGTGTCCTACCAGCAAGGG......PBL
CTTTACCTCGGTGTCCTACCAGCAAGGG......SW480
CTTTACCTCGGTGTCCTACCAGCAAGGG......SW620
```

B

```
    1          11         21         31         41         51         61         71
TGGGGCTACGGCTGATCTATTTCTCATATGATGTTAAAATGAAAAAAGGAGATATTCCTGAGGGTACAGTG
TGCGGCTACGGCTGATCTATTTCTCATATGATGTTAAAATGATAGAAAAAGGAGATATCCCTGAGGGTACAGTG
TGCGGCTACGGCTGATCTATTTCTCATATGATGTTAAAATGATAGAAAAAGGAGATATCCCTGAGGGTACAGTG
TGCGGCTACGGCTGATCTATTTCTCATATGATGTTAAAATGATAGAAAAAGGAGATATCCCTGAGGGTACAGTG
TGCGGCTACGGCTGATCTATTTCTCATATGATGTTAAAATGAAAGAAAAAGGAGATATCCCTGAGGGTACAGTG 81         91        101        111
TCTCTAGAGAGAAGGAGGAGCGCTTCTCCCCTGATTCTG......PBL
TCTCTAGAGAGAAGGAGGAGTGCTTCTCCCCTGATTCTG......SW480
TCTCTAGAGAGAAGGAGGAGTGCTTCTCCCCTGATTCTG......SW620
TCTCTAGAGAGAAGGAGGAGTGCTTCTCCCCTGATTCTG......SW620
TCTCTAGAGAGAAGGAGGAGTGCTTCTCCCCTGATTCTG......COLO205
```

FIG. 16

FIG. 17
A  – 72 SYK
– 70 SYK-B
B 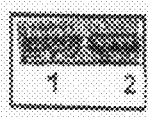 – 72 SYK
– 70 SYK-B

METHODS FOR IDENTIFYING OR DIAGNOSING CARCINOMA CELLS WITH METASTATIC POTENTIAL BASED ON THE MEASUREMENT OF LYMPHOID GENES OR THEIR PRODUCTS IN CARCINOMA CELLS

This application is a continuation of application Ser. No. 10/939,764, filed Sep. 13, 2004, now abandoned which is a divisional of U.S. patent application Ser. No. 09/110,376, filed May 12, 1998 (now U.S. Pat. No. 6,790,604), the disclosures of which are incorporated herein by reference.

SEQUENCE LISTING

Appended hereto is a paper copy (4 sheets) of the Sequence Listing for the sequences in FIG. 16 of the drawings. Applicant requests the use of the compliant computer readable "Sequence Listing" that is already on file for the prior application Ser. No. 10/939,764, filed Sep. 13, 2004, and the appended paper copy (4 sheets) of the "Sequence Listing" in this application is identical to the computer readable copy (floppy disc) filed for the other application Ser. No. 10/939,764 and which was submitted with an Amendment and Response to Notice to File Corrected Application Papers mailed Jan. 18, 2005, in that other application. The appended "Sequence Listing" and the computer readable copy referred to above are incorporated herein by reference and contain no new matter.

FIELD OF THE INVENTION

The present invention relates to methods for distinguishing human solid non-lymphoid tumor cells with lymphotrophic metastatic potential from those without this property and for treatment thereof.

BACKGROUND OF THE INVENTION

Metastasis or the spread of primary tumor cells to a secondary organ is a complex process involving a cascade of steps (Paget, S., 1889, *Lancet,* 1:571-573, Fidler, I. J., 1990, *Cancer Res.* 50:6130-6138). Neoplastic transformation usually results in the dedifferentiation of pre-malignant cells. Consequently, there is a loss of cell-to-cell adhesiveness and a detachment of tumor cells from the primary tumor bed. However, detachment does not ensure the spread of primary tumor cells to distant sites, since tumor cells must also acquire migratory capability to invade a secondary organ (Fidler, I. J., Kripke, M. L., 1977, *Science* 197:893-895). More specifically, tumor cells must have target specific motility and preferential chemotaxis to direct them toward either blood vessels (hematogenous metastasis) or lymphatics (lymphotrophic metastasis) (Willis, R A. 1972. 3rd Edit. London: Butterworth). It is our hypothesis that primary tumor cells may become metastatic by acquiring the phenotypic properties of migrating T lymphocytes. Once they acquire this invasive phenotype, these T cell "like" solid tumor cells can either be swiftly carried away by blood flow or may roll through lymphatic channels (Imhof, B. A., Dunon, D., 1995, *Adv. Immunol.* 58:345-416). Migration of tumor cells is promoted by specific receptor/ligand interactions between the tumor cells and cells lining the endothelium of secondary sites (Weiss et al., 1988, *FASEB J.* 2:12-21; McCarthy et al., 1991, *Sem. Cancer Biol.* 2:155-167) where arrest and adhesion of tumor cells occurs. Here the tumor cells may die, become dormant, or invade the organ's parenchyma where they proliferate and undergo homeotypic aggregation (Yefenof et al., 1993, *Proc. Natl. Acad. Sci.* 90:1829-33; Cohen et al., 1995, In: NK Cells in the Liver, Bouwens L, ed. RG Landes Biomedical Publication, Austin, CRC Press. Pp. 71-100). Tumor cells use growth factors produced by the tumors themselves (autocrine) or by cells from the secondary organs (paracrine) for colony growth and survival (Radinsky, R., 1992, *Cancer Metas. Rev.* 12:345-361).

In accordance with this specification and claims, tumor cells may be classified as benign if they have not invaded surrounding tissue and malignant if they have done so, and malignant tumor cells may be classified as having metastatic potential if they have the capacity to spread through the lymph or blood systems to distant sites and to have non-metastatic potential if they do not have such capacity. If metastatic cells have the capacity to spread through the lymph system, they are defined herein and in the claims as having "lymphotrophic" metastatic potential. A "primary" tumor is defined, for the purpose of this specification and the claims as one which is located at its site of origin, i.e., before any metastasis thereof, as contrasted with a "secondary" tumor, which is a tumor located at a site to which the primary tumor has metastasized.

Metastasis presents a cancer clinician with great difficulty in diagnosing and treating the malignant tumor because (i) metastasis may comprise as little as one or a few cells thereby evading clinical diagnosis even with modern techniques; (ii) often metastasis has already been seeded by the time a patient is diagnosed with a malignant non-lymphoid solid tumor (Silverberg et al., 1989, *CA Cancer J. Clin.* 39:3-21); (iii) treatment is more complex than simple surgical excision of the primary tumor; (iv) systemic therapy for metastatic non-lymphoid solid tumors, such as renal cell carcinoma (Rosenberg et al. 1985, *N. Engl. J. Med.* 313:1485-1492) remains ineffective with little survival advantage; and (v) not all malignant tumors have the same metastatic potential and no direct relationship has been established in determining whether any particular carcinoma will develop metastasis.

Monoclonal antibodies (Mab) have been used to characterize and classify T cell surface molecules such as the clusters of differentiation (CD) of human leukocyte antigens. As illustrated in FIG. 1, the T cell receptor (TCR), illustrated at 20, is an integral membrane protein, expressed on the surface of T lymphocytes, illustrated at 22, occurring as a disulfide linked heterodimer that is non-covalently associated with CD3 chains, illustrated at 24. TCR has been linked to autoimmune disease and anti-TCR antibodies have shown therapeutic potential for treating autoimmune disease (Basi et al., 1992, *J. Immunol. Meth.* 155:175-191). In some cancers, a correlation exists between an increase in concentration of the TCR associated CD8 molecule in the serum of children with non-Hodgkins lymphoma and the stage of the disease and its responsiveness to therapy (see U.S. Pat. No. 5,006,459).

Several studies have shown that T cell-associated molecules (Omar et al. 1991, *AIDS* 5:275-281, Kawami et al., 1993, *Biotherapy* 6:33-39; McMillan et. al. 1995, *Int. J. Cancer* 60:766-772) are expressed on the surface of non-lymphoid solid human tumor cells. SW620, a metastatic human colon tumor-derived from the lymph node of a 51-year-old male has been shown to possess the TCR co-receptor CD4 on its surface by several different methods including Northern analysis and FACS (Omary et al 1991. *AIDS* 5:275-281). To date, no one has directly identified Vβ sequences on the surface of carcinoma cells.

SUMMARY OF THE INVENTION

The present invention is related to our belief that the acquisition of lymphotrophic metastatic potential by such transformed cells is accompanied by their ability to express aberrant lymphoid specific genes or their products including germline CTβ, germline Vβ and their related TCR associated genes or their products and TCR associated signal transduction genes or their products. More specifically, the determination of the percentage of cells of a solid non-lymphoid tumor expressing lymphoid gene products including, but not limited to, the following three categories of closely related lymphoid specific genes or their products: Category 1, (germline CTβ, germline Vβ variants); Category 2 (TCR associated molecules; CD3ε, CD4, CD7, CD8) and Category 3 (T cell-derived signal transduction molecules; CD3ζ, p56 type 1, p59 type T, ZAP-70, and SYK) is used, in accordance with the present invention, to identify lymphotrophic metastatic potential. As used herein and in the claims, the term "lymphoid gene products" is meant to include the lymphoid genes as well as the products thereof.

Accordingly, an object of the invention is to predict the lymphotrophic metastatic potential of a solid non-lymphoid tumor.

Another object of the present invention is to provide treatment for such a tumor.

In order to predict the lymphotrophic metastatic potential of a solid non-lymphoid tumor, in accordance with the present invention, a plurality of representative samples of the tumor are obtained and the percentage of cells in each of the samples which express lymphoid gene products is determined, wherein the metastatic potential of the tumor is predicted to be low when a low percentage of tumor cells in all of the samples are detected to express lymphoid gene products and predicted to be high when a high percentage of tumor cells in at least one of the samples are detected to express lymphoid gene products.

In order to predict the lymphotrophic metastatic potential of a primary solid non-lymphoid tumor, in accordance with the present invention, cells from the tumor are injected subcutaneously into at least one anti-AsGMl-treated (NK depleted) nude animal (such as a nude mouse) and the animal examined for tumors at sites other than the site of the injection.

In order to treat a solid non-lymphoid tumor, in accordance with the present invention, a substance comprising a therapeutically effective amount of a molecule linked to a toxin, radionuclide, or chemotherapeutic agent and having binding specificity for a tumor-specific lymphoid gene product idiotype is systemically administered.

The above and other objects, features, and advantages of the present invention will be apparent in the following detailed description of the preferred embodiment thereof when read in conjunction with the accompanying drawings wherein the same reference numerals denote the same or similar parts throughout the several views.

BRIEF DESCRIPTION OF THE DRAWINGS

FIG. 16 is a view of DNA sequences of PCR products generated in FIG. 15 from human colon tumor cell line and peripheral blood leukocyte cDNA using (A) CTβ primers (CTβS1 and CTβAS1, 290 bp) and (B) Vβ3S1 primers (VβNS4 and VβNAS4, 153 bp). Sequences represent cDNA amplified between but not including primers. Asterisk (*) denotes base deviation of human colon tumor PCR products from that of peripheral blood leukocytes.

FIG. 17A is a view of a western blot of SYK (anti-human SYK) from Lane 1: Jurkat; Lane 2: SW480; Lane 3: SW480E; Lane 4: SW480R and Lane 5: SW620 cell lines. SYK is 72 kDa. Note presence of the 70 kDa isoform of SYK in SW480E cells.

FIG. 17B is a view of a western blot of SYK (anti-human SYK) from Lane 1: Jurkat; Lane 2: SW480E.

DETAILED DESCRIPTION OF THE PREFERRED EMBODIMENTS

Figure 1:
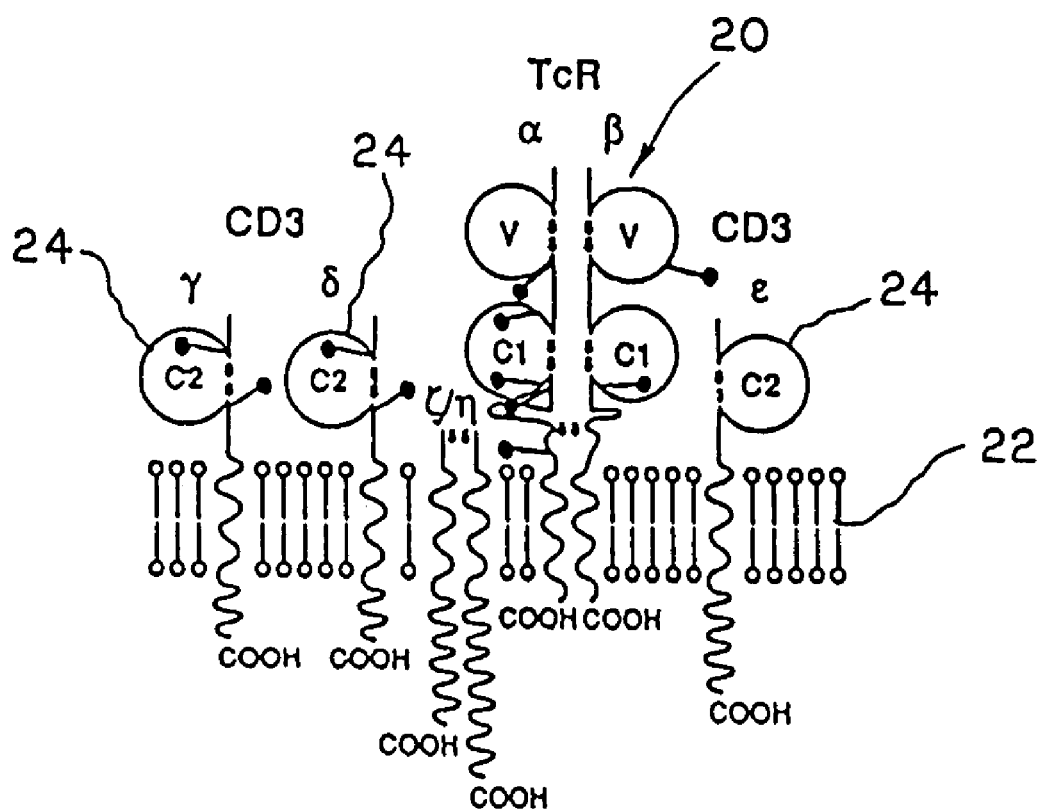
FIG. 1 is a schematic view of the structure of TCRα/β.
Figure 2:
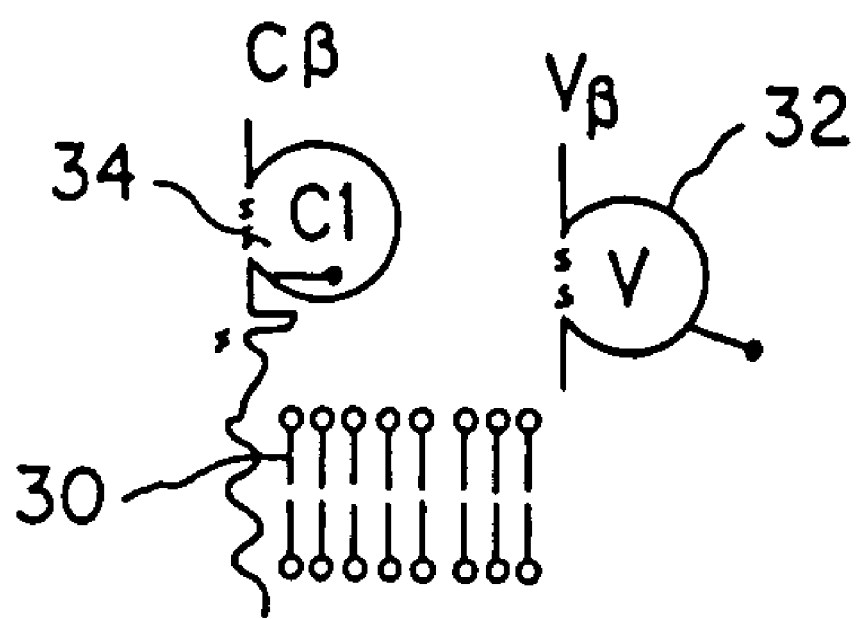
FIG. 2 is a view similar to that of FIG. 1 of the predicted surface expression of germline CTβ and Vβ on non-lymphoid solid tumor cells (surface orientation of Vβ unknown).

FIG. 2 illustrates at 30 a tumor cell wherein germline or unrearranged Vβ gene and Cβ transcripts, illustrated at 32 and 34 respectively, are expressed on the tumor cell surface, as discussed in greater detail hereinafter. Other lymphoid gene products may also be expressed on the tumor cell surface. Since very few somatic mutations are found in T cell clones or T cell lines, Vβ may be an excellent target for diagnosis and immunotherapy. In this regard, Vβ6 positive syngeneic T cell tumors can be inhibited from growing by administering anti-mouse Vβ6 to mice (Kanagawa et al., 1989, J. Exp. Med. 170:1513-1521). Interestingly, the anti-tumor treatment of mice bearing T cell tumors by anti-Vβ antibody does not compromise the immune status of the mouse despite the fact that a significant proportion of peripheral T cells are eliminated by the treatment. In another study, one-third of Vβ chains were genetically deleted in certain mouse strains causing a deficit in the expressed repertoire of TCR without jeopardizing immune potential (Kanagawa et al. 1989, *J. Exp. Med.* 170:1513-1521). Since the number of genes encoding known Vβ segment is limited, the epitopes expressed on a Vβ gene product from normal cells can be used as a target molecule for monoclonal antibody diagnosis and therapy of solid tumors expressing Vβ chains. Further, there is a bias for certain Vβ genes. Vβ is dispersed throughout the gene locus and represents a wide range of post selection utilization, from abundantly expressed Vβ8 to those that are rarely expressed such as Vβ5. Selected expression would not be expected in the precursor population before surface expression of Vβ. It would seem reasonable to establish panels of antibodies specific for each Vβ gene segment for use in diagnosis and therapy of carcinomas expressing clonally distributed germline Vβ genes.

Normally, epithelial cells including primary neoplastic cells do not migrate. However, there are cells in the body whose function is to migrate to distant organs. These migrating cells are members of the immune system and include immature or pre-T bone marrow cells, immature or pre-T thymocytes, T cells, B cells and macrophages and others. Without wishing to be bound by theory here or elsewhere in this application, we believe that the lymphoid specific genes from these migrating cells can convert or allow the progression of nonmetastatic carcinoma cells into potentially metastatic carcinoma cells. There are at least three mechanisms by which this phenomena may occur. Kim et al. (1993, *Proc. Am. Assoc. Cancer Res.* 34:63A) have successfully converted primary nonmetastatic non-lymphoid mammary rat tumor cells (NM-081) into metastatic tumor cells (NMT-2) that carry TCR associated molecules by fusing them with thymocytes (Table 1). These "converted" metastatic NMT-2 mammary tumor cells can metastasize to the lymph nodes of mice. The nonmetastatic NM-081 mammary tumor cells do not express T cell associated markers while the metastatic NM-T2 cells express CD8 and Thy 1 on their surface. On the other hand, NM-081 fused with macrophages converted these mammary tumor cells into metastatic cells (NM-M2) that metastasized to the lungs.

Conversely, expression of lymphoid genes in tumor cells may arise from derepression, as proposed by Helmericks and Rosen. Helmericks and Rosen (1995, *J. Biol. Chem.* 270: 27538-27543) have shown that 35 kDa and 75 kDa repressive molecules bind to the 5' promoter region (−520 to −460 kb) of the p56$^{lck}$ gene and inhibit the expression of this T cell-associated signal transduction molecule in human colon cancer cell lines such as HT-29, T84 and Hela cells. In contrast, when these repressive molecules are absent (i.e., COLO205 colon tumor cells), the tumor cells can express the p56$^{lck}$ type 1 (thymocyte) gene product. In another study, McCracken et al (Oncogene, 1997, 15:2929-2937) demonstrated that p56$^{lck}$ type 1 promoter in Hela cells could be activated when the tumor cells were transfected with ETS-1 and Sox-4 transcription factors.

Finally, there have been reports that lymphoid cells can penetrate the cytoplasm of tumor cells where they remain viable (Radosevic et al. 1995, *Cytometry* 20:273-278). This process has been termed emperiopolesis. Emperiopolesis of lymphocytes in tumor cells has also been observed. See Tsunoda et al. 1992, *Virchows Archiv* 62:69-74. Although which mechanisms actually causes conversion of nonmetastatic carcinoma cells to T cell "like" carcinoma cells are unknown, we believe that the outcome is the same. i.e., the lymphoid gene program can convert epithelial nonmetastatic carcinoma cells into metastatic carcinomas. Additionally, these three mechanisms are not necessarily mutually exclusive (Mayer et al., 1993, *Int. J. Oncol.* 3:366-372). Further, it should be possible to "read" the lymphoid program expressed on the non-lymphoid T cell "like" solid tumor cell surface and predict, (i) whether the tumor cells are potentially metastatic, (ii) the number of potentially metastatic tumor cells in the primary bed and (iii) the secondary site or sites where the tumor cells may travel. It appears that tumor cells expressing lymphoid properties travel to the lymph nodes via the lymphatics while tumor cells expressing macrophage properties go to the lungs via the blood stream (see Table 1).

Lymphoid cells and metastatic tumors migrate preferentially to certain organs and even prometastatic territories (zones) within the same organ. For example, colon tumors tend to metastasize to the lymph nodes and liver, breast tumors to the lymph nodes and prostate cancer to the bones. Infiltrating T lymphocytes involved in hepatitis and metastasizing colon tumor cells are arrested in the periportal region or zone 1 of the liver lobule (Vidal-Vanaclocha et. al. 1993, *Sem. Liver Disease* 13:60-67). More important, cancer cells arrested in zone 1 of the liver lobule remain and develop metastatic foci while tumor cells that migrate to the pericentral region or zone 3 do not form colonies (Barbera-Guillem. et al. 1989, *Cancer Res.* 49: 4003-4010). Similarly, infiltrating CD4$^+$ T cells remain in zone 1 while CD8$^+$ T cells redistribute throughout the organ (Cohen S. A. et al. 1996. In: Natural Killer Cells in the Liver, ed. Bouwens L, RG Landes Biomedical Publishers, Austin, CRC Press. pp. 71-100). These CD4$^+$ T cells resemble hematopoietic colony forming cells that also only develop colonies in zone 1. When metastatic tumor cells and colony forming cells are simultaneously arrested in zone 1, augmented growth of both cell populations occurs (Vidal-Vanaclocha et al. *Int. J. Cancer* 46:267-271) suggesting that these cell types share and respond to common ligands and growth factors using similar or identical receptors. Colon and breast carcinoma tumor cells can express CD4 on their surface. It has been demonstrated that CD4$^+$ T cells with a phenotype that was CXCR4$^+$, CD26$^-$, CD45R0$^-$ and CD45RA$^+$ tend to migrate to lymph nodes while T cells with a phenotype that was CCR5$^+$, CD26$^+$, CD45R0$^+$ and CD45RA$^-$ migrate to peripheral tissue (Bleul et al. 1997, *Proc Natl Acad. Sci.* 94:1925-1930). CD4 bearing metastatic tumors would contain addresses that would preferentially direct them to zone one of the liver and lymph nodes. Thus, metastatic tumor cells are "piggybacked" to the site and masked behind a T cell "like" cover. The concept that migrating cells contain molecular addresses on their surface that can be read by molecules at their destination sites has been previously discussed (Rusoslahti E., 1996, *Sci. American* 275:72-77; Springer T. A., 1994, *Cell* 76:301-314).

The following examples demonstrate the detection of germline CTβ, germline Vβ and their related T cell-associated molecules on/in human and experimental tumors using one or more methods selected from the group consisting of fluorescence microscopy, fluorescence activated cell sorting (FACS), ELISA, ELISPOT, Western blot analysis, enzymatic amplification, nucleic acid sequencing. The human tumor cell lines were obtained as follows: Jurkats, SW480, SW620, BT474 (ATCC, Bethesda, Md.). Vβ3 expressing C7CH17 cells were obtained from the Imperial Cancer Center (London, England). SW480E and SW480R were supplied by Dr. I. B. Weinstein (Columbia University, NY, N.Y.). The rat tumor cell lines and human biopsies were supplied by Dr. U. Kim (Buffalo, N.Y.). All tumor cell lines were grown in plastic T-flasks in a humid atmosphere of 5% CO, in air, in adequate media supplemented with 10% FBS and containing penicillin and streptomycin. Anti-JOV1 and anti-JOV3 were obtained from Ancell Corp. of Bayside, Minn.

In order to insure that no lymphocytes or other leukocytes were in the samples tested as described herein, tumor cell lines, which are known to be devoid of lymphocytes or other leukocytes, were used, except that, where clinical samples were used, as in the Table 7 tests, FITC-labeled anti-EMA (anti-epithelial membrane antigen) antibody tumor marker was used to locate only the tumor cells to insure that products of lymphocytes or other leukocytes were not included in the assay. Other ways to prepare pure tumor cell populations (without lymphocytes or other leukocytes) include mixing Dynabeads magnetic beads coupled with anti-EMA antibody with the tumor cell suspension, as discussed in Latza et al, *J. Clin. Path.* 43:213-218, and in Naume et al, *J. Hematother.* 6:103-114 (1997). Cell viability is not affected by process and is suitable for immunocytochemical, PCR and RT-PCR analysis. Other antibodies may also be substituted such as (for Colorectal Cancer) HEA125 MAb, HT29-15 MAb; (for Breast Cancer) EMA Mab, B72.3 MAb, BCD-B4MAb, NCRC-11 MAb; (for Prostate Cancer) anti-PSA antibody, PD41MAb and; (for Lung Cancer) ALT-04 MAb.

The tumor biopsies or surgical specimens discussed hereafter were obtained, purified as above to insure that no lymphocytes or other leukocytes were included in the assays.

Tumor cells were detached by brief exposure to 0.1% Trypsin plus 2 mM EDTA, then incubated for 48 hours in spinner-flask in media plus 10% FBS at 5% $CO_2$. After extraction and quantification of the mRNA (shown to be intact by 0.7% agarose gel electrophoresis), a total of 20 μg of purified RNA was separated on a 1.2% agarose gel containing 22 M formaldehyde. The electrophoresis was performed at 80V. The tracks containing the molecular size standard was cut off the gels and the migration distances were measured. The gels were rinsed and transferred onto nitrocellulose filter. Expression of Vβ mRNA can be detected by extracting and purifying mRNA from nonolymphoid tumor cells and then subjecting the purified mRNA to enzymatic amplification to obtain sufficient quantities for analysis and detection. Enzymatic amplification techniques which could be employed include those known in the art such as PCR (polymerase chain reaction) and nucleic acid sequence-based amplification. Detection of the amplified nucleic acid includes techniques known in the art including, but not limited to, agarose gel electrophoresis, northern blotting, fluorescence-based hybridization assays, chemiluminescence-based hybridization assays, and captures hybridization microtiter assays. Oligonucleotides primers and probes can be synthesized from the nucleic acid sequence of the Vβ's. Probes can be synthesized with methods known to those skilled in the art to incorporate either non-isotopic or isotopic label. Alternatively, the label may be incorporated directly into the amplified product In this example, single-stranded cDNA, obtained by reverse transcription from the extracted tumor cell mRNA, was amplified by PCR™ utilizing primers for Vβ genes from commercial sources. The amplified products were separated on a 1.2% agarose gels and stained with ethidium bromide in parallel with positive and negative controls.

Tumor biopsies or surgical specimens, purified as discussed above, were isolated and prepared for confocal Immunofluorescence microscopy or for FACS. After being washed, the carcinoma cells were incubated for 30 minutes at 4° C. in a solution of PBS, fixed with 1% paraformaldehyde, and analyzed within 48 hours using confocal microscopy or FACS. Quantitative analysis of Vβ expression and other markers on tumor cells was performed using either of these methods.

Tumor biopsies or surgical specimens purified as discussed above, were isolated and tumor cell lysates were prepared for Western analysis. For analysis $5×10^6$ tumor cells or control cells were collected into PBS containing 1 mM PMSE. After washing, cells were homogenized in buffer 10 mM Tris-HCl pH 7.4, containing 0.25 M sucrose, 1 mM $MgCl_2$, 5 mM $CaCl_2$, and a mixture of protease inhibitors. Polyacrylamide gel electrophoresis was performed. The protein was transferred onto nitrocellulose filters by electrophoretic transfer for 2 hours at 40 V. The filter was then incubated in avidin blocking solution with 3% normal human serum, following three washes with TTBS. The mouse anti-human antibodies (CD3ζ, p56, p59, ZAP-70, SYK) added at a 1:40 dilution in TTBS and incubated for 2 hours. After three washes, a biotinylated rabbit-anti mouse IgG was added at a 1:200 dilution in TTBS for 1 hour. Following three washes with TTBS, the blot was incubated with avidin and biotinylated horseradish peroxidase for 30 minutes. The blot was then incubated with DAB and the sites of antibody binding were revealed by brown precipitate. The molecular weight (MW) marker proteins were: beta-galactosidase (116 Kd), Bovine albumin (66 Kd), Egg albumin (45 Kd) and carbonic anhydrase (29 Kd).

Murine MCA-26 colon tumor cells, MCA-38 colon tumor cells and B16F10 melanoma cells were cultured, RNA extracted and tested for mRNA using a human CTβ probe (see below). RNA from ConA activated splenic T cells gave a normal 1.35 and truncated 1.0 kb message for CTβ. In contrast, the murine tumors gave a 1.1 kb message consistent with a truncated CTβ message (not shown). Davis (1990, *Ann Rev Biochem* 59:475-496) has shown that a truncated 1.0 kb message is found on non-tumor cells.

Figure 3:
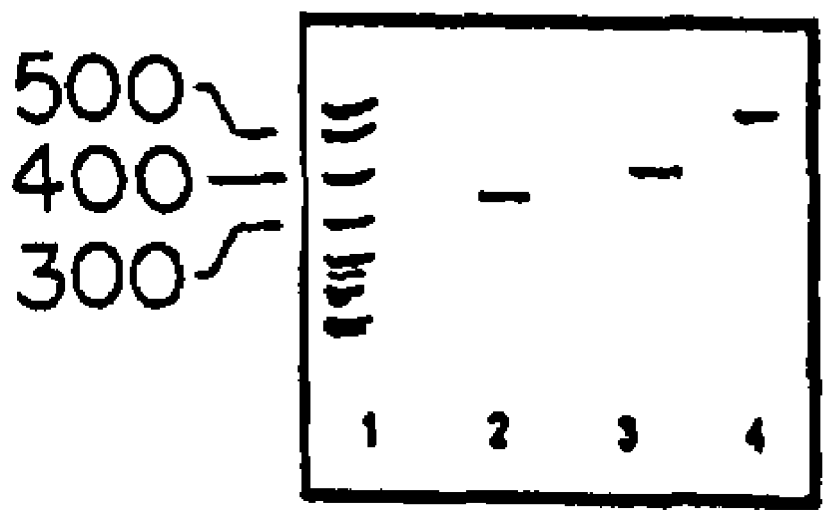
FIG. 3 is a view of the PCR analysis of MCA-26 tumor cells and Balb/c thymus cDNA. Primers Vβ8: sense primer in the variable region and CTβ-A1: anti-sense primer in the constant region, separated by 200-230 bp in the intact TCRβ transcript of thymus cells, were used to determine rearrangement of the 1.0 kb transcript in the colon tumor cell line, MCA-26. The thymus band of roughly 427 bp indicates the presence of a normally oriented single TCR β transcript containing both Vβ8 and CTβ mRNA. Note that the lack of such a band in the MCA-26 lane reflects the lack of a similar single TCR β transcript in MCA-26 cDNA. Lane 1: 100 bp ladder, Lane 2: cDNA from MCA-26 tumor cells (band at 366 kb), Lane 3: cDNA from Balb/c thymus (band at 427 kb), and Lane 4: actin cDNA control (band at 544 kb).

Murine colon MCA-26 cells were cultured, RNA extracted and tested for Vβ8 mRNA using the appropriate primers for Vβ8, and CTβ (see Candeias et al. 1994, *Eur J Immunol.* 24:3073-3081 for primer sequences). As shown in FIG. 3, RNA from Balb/c thymocytes gave a band at 427 kb consistent with a rearranged Vβ8 message. In contrast, RNA from MCA-26 colon tumor cells gave a band at 366 kb that was consistent with an unrearranged germline Vβ8 message.

Figure 4:
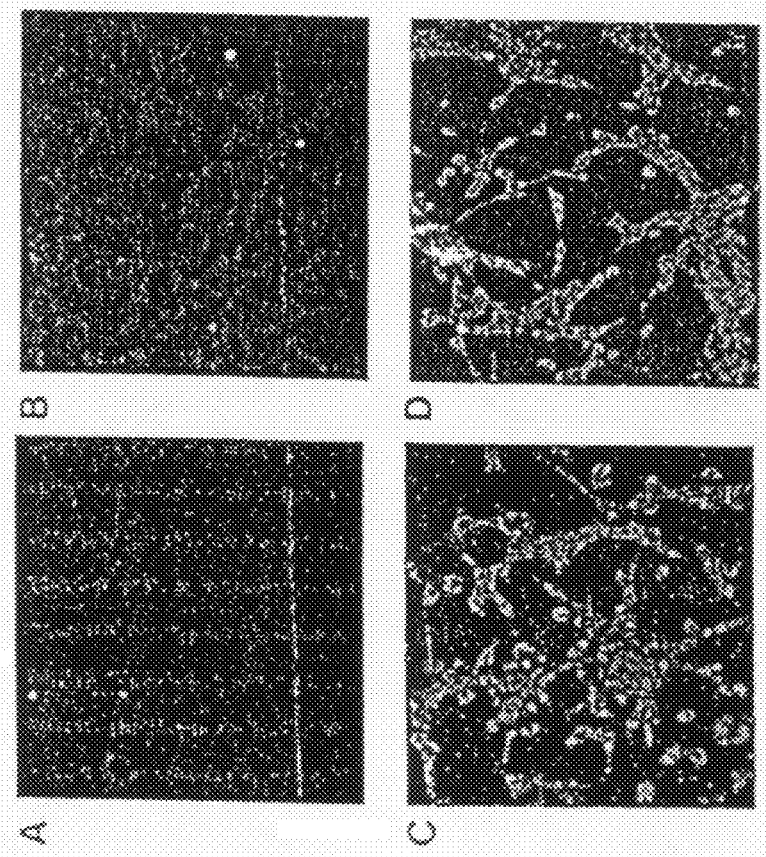
FIG. 4 is an immunofluorescence view of MCA-26 tumor cells with: A) Fl-anti-mouse Ig control, B) Fl-anti-mouse V α3, C) Fl-anti-mouse TCRβ, and D) Fl-anti-mouse Vβ8.1/2 antibody.
Figure 5:
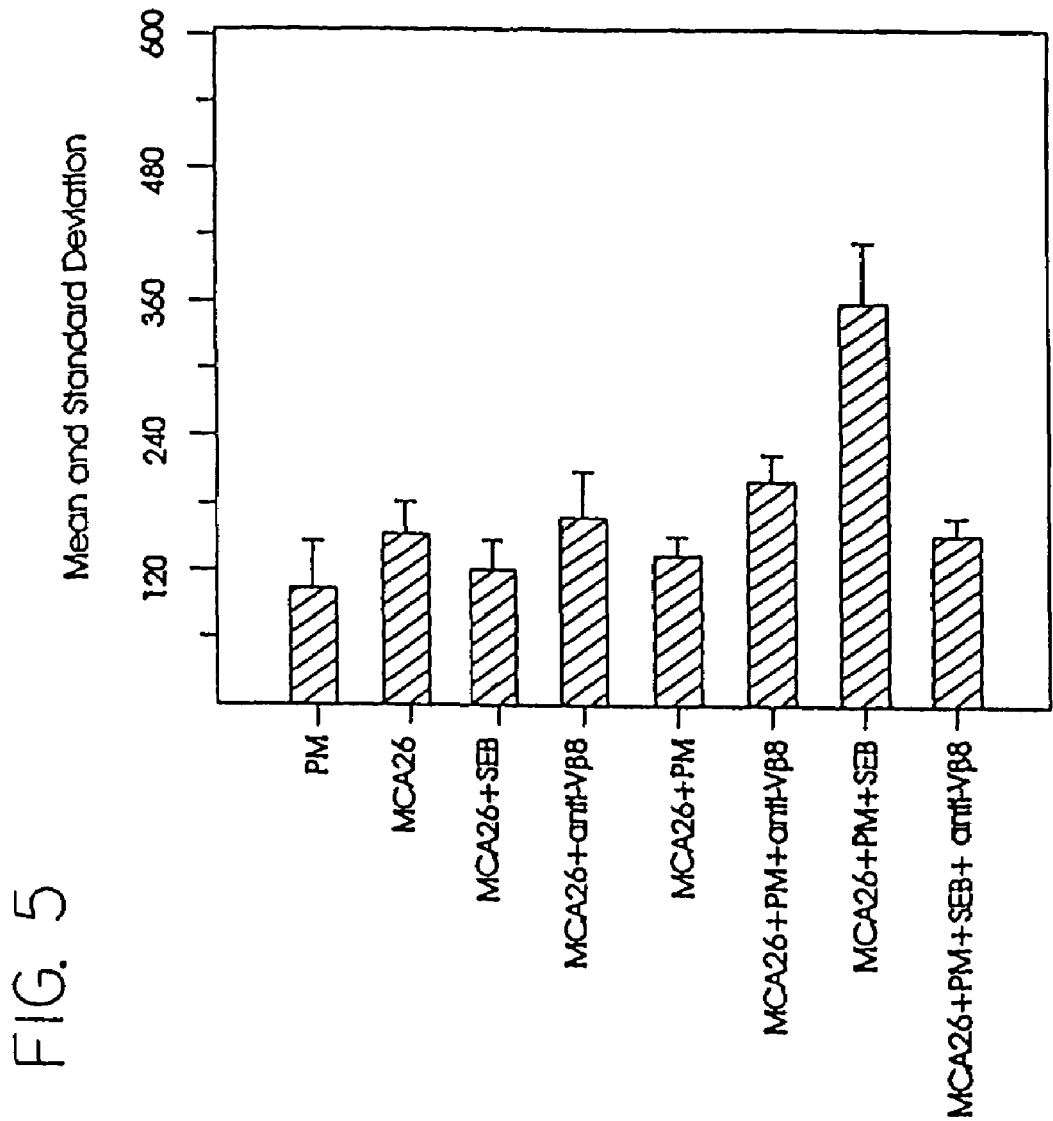
FIG. 5 is a graph illustrating proliferation of $10^4$ Balb/c peritoneal macrophages (PM); $5 \times 10^4$ MCA-26 tumor cells in serum free medium control; (1 µg/ml) SEB; SEB+anti-mouse Vβ8.1/2.1/2 (azide free); SEB+PM; SEB+PM+anti-mouse Vβ8.1/2; SEB+PM; SEB+PM+anti-mouse Vβ8.1/2 antibody. Cells were cultured in a 96-well plate for 72 h and pulsed with 1 µCi of 3H-Tdr for 6 h, harvested and cpm counted.

Using immunofluorescence, we have observed Vβ8.1/8.2 and TCRαβ on the surface of murine MCA-26 colon tumor cells (FIG. 4). In contrast, the tumor cells were not stained for the isotype control and Vα3. SEB is a superantigen that can bind to the Vβ chain on the T cell receptor and trigger these cells to divide (Lamphear et al., 1998, *J. Immunol.* 160:615-623). MCA-26 colon tumor cells expressing a putative Vβ8 receptor were stimulated in serum free conditions with peritoneal macrophages pulsed with SEB, and the tumor cells underwent increased proliferation (FIG. 5). The proliferation of the stimulated tumor cells was blocked by the addition of azide free anti-Vβ8.1/8.2 suggesting that tumor-derived germline Vβ could be ligated by the superantigen, SEB, to induce a transduction signal through the Vβ chain. Similar results were observed with MCA-38 colon tumor cells. Table 2 is a summary of results demonstrating the expression of TCRβ and other lymphoid gene products on the surface of various murine carcinoma cell lines. The more metastatic the tumor cells the higher expression of TCRβ on their surface.

We have developed a panel of seven syngeneic rat mammary tumor cell lines that progress from estrogen dependent to independent over a 20-year period (Table 3A). These tumor cell lines were in different states of differentiation. Interestingly, the least differentiated (MTW9B, MTW9C, MTW9D) were not metastatic while the metastatic tumors (MT449, MT450) were among the most differentiated. These primary rat mammary tumor cell lines (MT449, MT450) were capable of invading the lymph nodes as well as other organs. More important, only the metastatic tumor cell lines expressed either of the lymphoid gene products; CD4 or CD8 (Table 3A and 3B).

Figure 6:
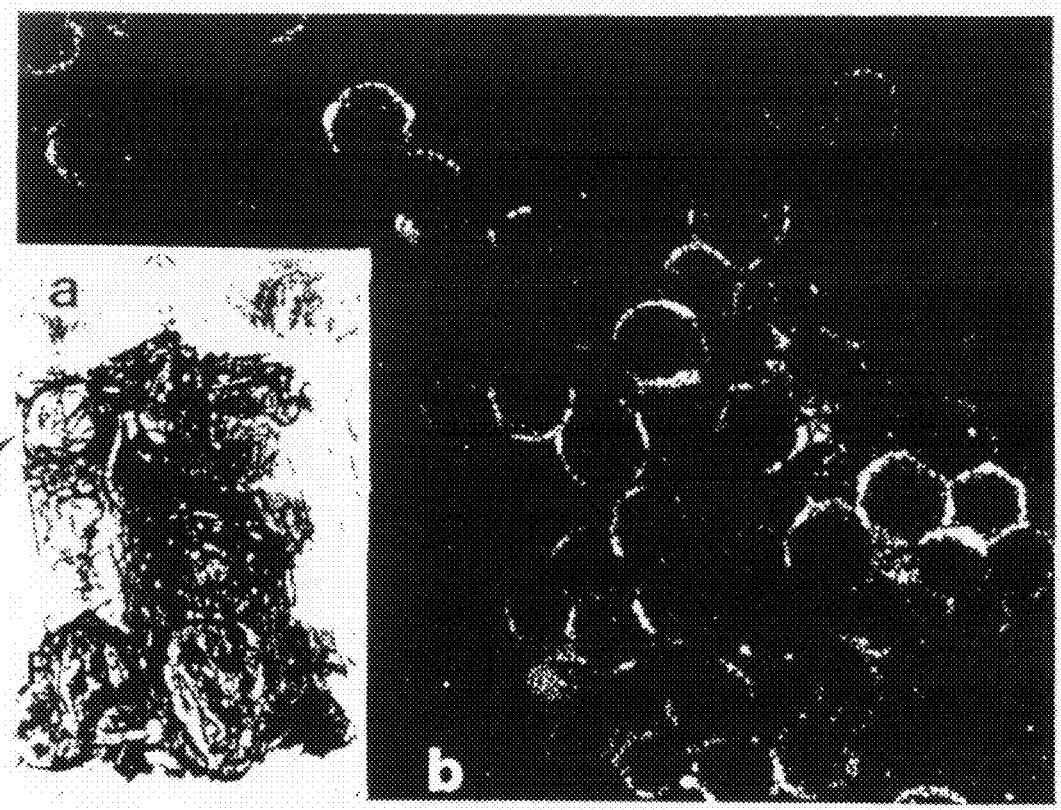
FIG. 6a is a view of local growth (primary tumor illustrated at P) and massive, generalized lymph node metastasis (illustrated at M) of SMT-2A rat breast tumor cells after sc injection in W/F rats.
FIG. 6b is a view of the SMT-2A tumor cells immunocytochemically stained with mouse monoclonal antibody specific to the rat CD8 T-cells, the secondary antibody being labeled with FITC.

Some human tumors can be successfully xenografted in athymic nude mice after growing them in vitro, but they seldom metastasize (Fogh et al. 1982, In: Proceedings of the 3$^{rd}$ International Workshop on Nude mice, Gustav Fisher, NY, pp. 447-456; Kim et al. 1984, In: Proceedings of the 4th International Workshop on Immune-deficient animals, S. Karger, Basel, pp. 235-238). The nonmetastatic MT-100 rat breast tumor after subcutaneous injection form local tumors in Wistar/Furth (W/F) rats and athymic nude mice (not shown). In contrast, the metastatic rat TMT-081 rat breast tumor after subcutaneous injection formed local tumor and metastasized to the lymph nodes in W/F rats but did not form tumors in nude mice (not shown). When these same nude mice were treated with anti-lymphocytic serum (ALS), the TMT-081 tumor began to grow and metastasize. If anti-ALS treatment was discontinued, the tumor ceased growing and began to scar. Thus, a lymphocyte population prevented the growth of metastatic tumors in nude mice when continuously present. In another series of experiments, nonmetastatic MT-W9B rat breast tumors grew locally in nude mice after sc injection. However, the metastatic SMT-2A rat breast tumors did not grow in nude mice (not shown). However, these tumors grew locally and metastasized in syngeneic W/F rats (FIG. 6A). Further, these metastatic rat tumor cells expressed CD8 on their cell surface (FIG. 6B).

Figure 7:
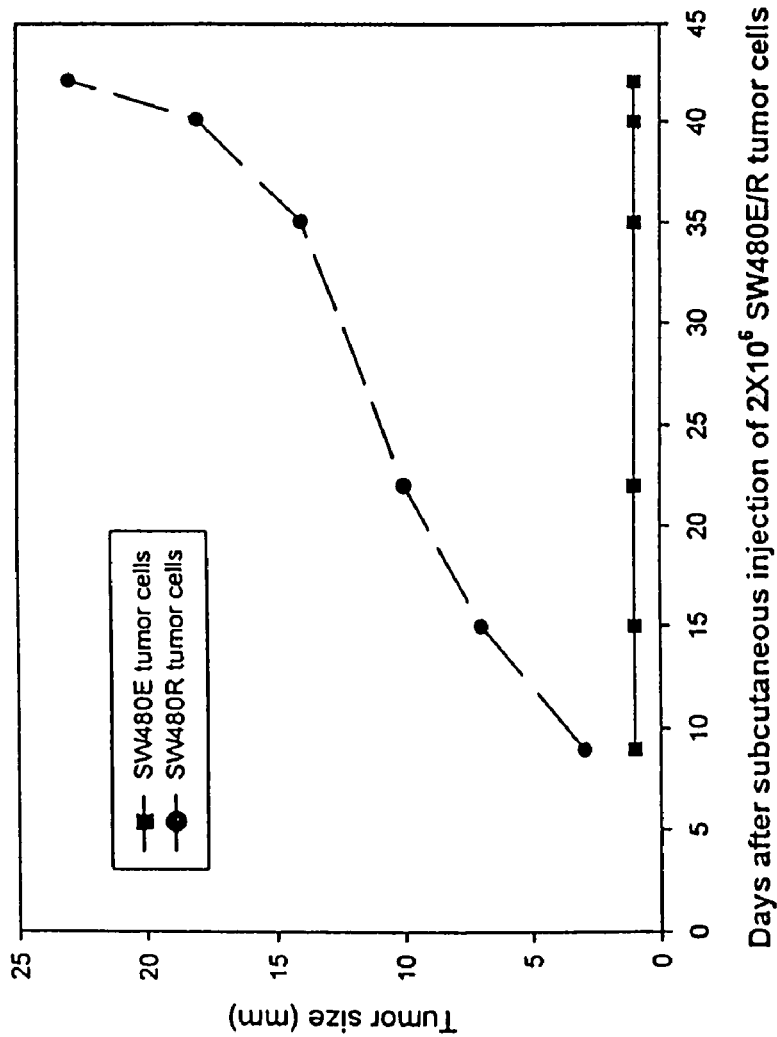
FIG. 7 is a graph showing growth kinetics of metastatic SW480E colon tumor cells vs. growth of nonmetastatic SW480R colon tumor cells after sc injection of $2 \times 10^6$ tumor cells in athymic nude mice.
Figure 8:
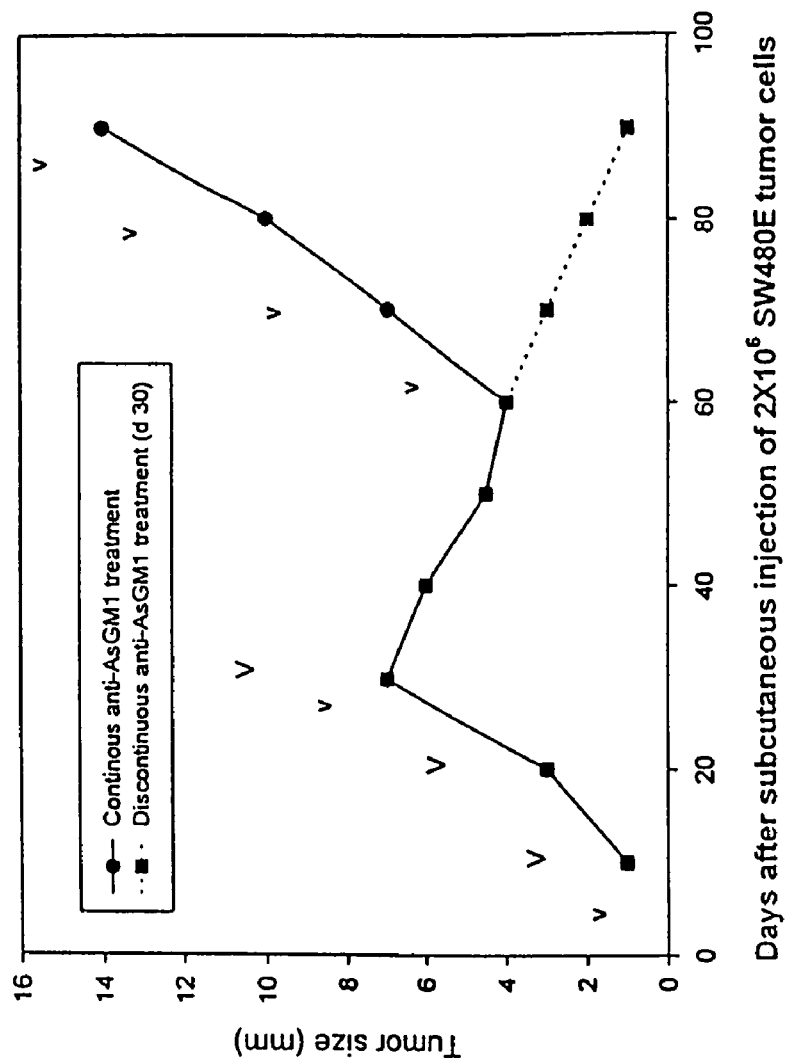
FIG. 8 is a graph showing growth kinetics of metastatic SW480E colon tumor cells after sc injection of $2 \times 10^6$ tumor cells into continuously treated anti-AsGM1 nude mice or discontinuously (at day 30) treated anti-AsGM1 nude mice, and further showing that tumor growth declines when anti-AsGM1 treatment is ceased on day 30.

SW480 is a primary Dukes C colon carcinoma cell line derived from a 50-year-old male patient. One year later, the same patient developed lymph node metastasis. SW620 is the cell line derived from that lymph node lesion. Two lines from SW480, were cloned namely; SW480E and SW480R tumor cells (Tomita et al., 1993, *Cancer Res* 52:6840-6847). The properties of the primary tumor, the two subclones, and the lymph node metastasis are listed in Table 4. When SW480R cells were injected subcutaneously into nude mice without NK depletion, a large local tumor grew but no metastasis was detected. In contrast, SW480E cells gave little local growth and were not metastatic (FIG. 7). The SW480E cells were motile in vitro. In contrast, SW480R cells proliferated more than SW480E in vitro but were much less motile in vitro. Since nude mice contain highly efficient NK cells (Cohen et al. 1990, *Cancer Res* 50:1820-1828), this is believed to mean that these potentially metastatic SW480E cells are NK sensitive. Therefore, when nude mice were treated with anti-AsGM1 to abrogate their NK cells, these SW480E tumor cells not only grew locally (FIG. 8) but also metastasized to the lymph nodes. The withdrawal of anti-AsGM1 treatment on day 30 led to the cessation of tumor growth, as shown in FIG. 8.

Figure 9:
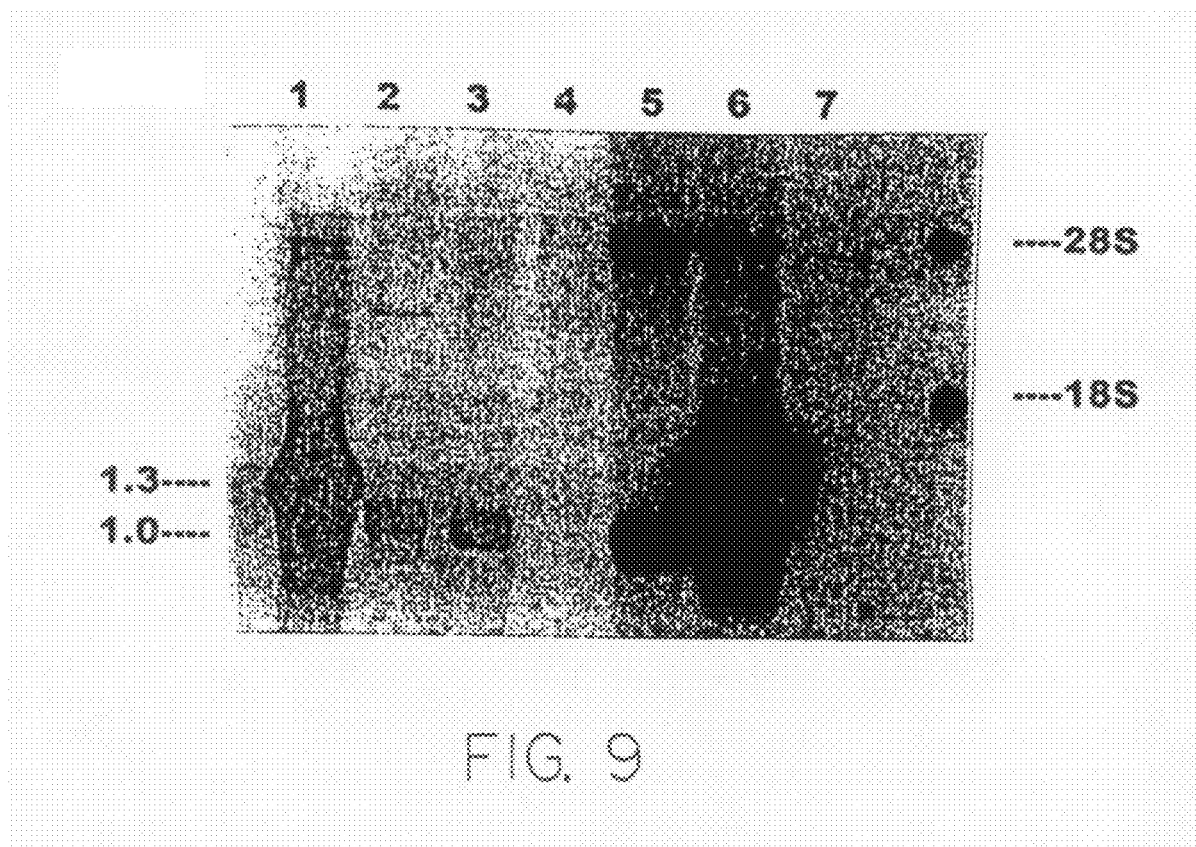
FIG. 9 is a view of a Northern blot analysis of human tumor cell line RNA. Human tumor cell lines were grown in 100 mm tissue culture dishes containing RPMI 1640 media supplemented with 10% FBS and 50 µg Gentamicin until semiconfluent. Total RNA was extracted, resolved through agarose, and hybridized to the 400 bp consensus sequence of the constant region of the human T cell receptor β (400 bp CTβ probe). Poly-A mRNA was either purchased or obtained by passage of total RNA across a poly-T column. Blots were re-probed with TPI. The motility of rearranged intact TCRβ is roughly 1.3 kb in functional mature T cells. Lane 1: poly A mRNA from the MOLT-4 cell line, Lane 2: poly A mRNA from SW480, Lane 3: poly A mRNA from Raji, Lane 4: poly A mRNA from the colon tumor derived cell line COLO205, Lane 5: total RNA from SW620, Lane 6: total RNA from Jurkat cells, Lane 7: total RNA the from colon tumor derived cell line HT29.

Using a 400-bp consensus sequence for the constant region of TCRβ (CTβ), extracts of total RNA from a panel of human tumor cell lines were analyzed by Northern blots. FIG. 9 revealed the presence of the 1.0 kb CTβ chain message in some tumor cell lines examined. SW480 tumor cells expressed less of this message than SW620 cells. The metastatic subclone, SW480E cells expressed more CTβ message than the tumorigenic, nonmetastatic subclone, SW480R cells (not shown). Other human tumor cell lines; T84, LS174T, A549, T47D, Hela, HepG2 cell lines tested for the CTβ message were negative (not shown). SW948, a cell line from a grade III colon adenocarcinoma, was positive for the CTβ message. In contrast, other human colon tumor cell lines; COLO201, COLO205, COLO320 and DLD-1 were negative for CTβ mRNA (not shown).

Figure 10:
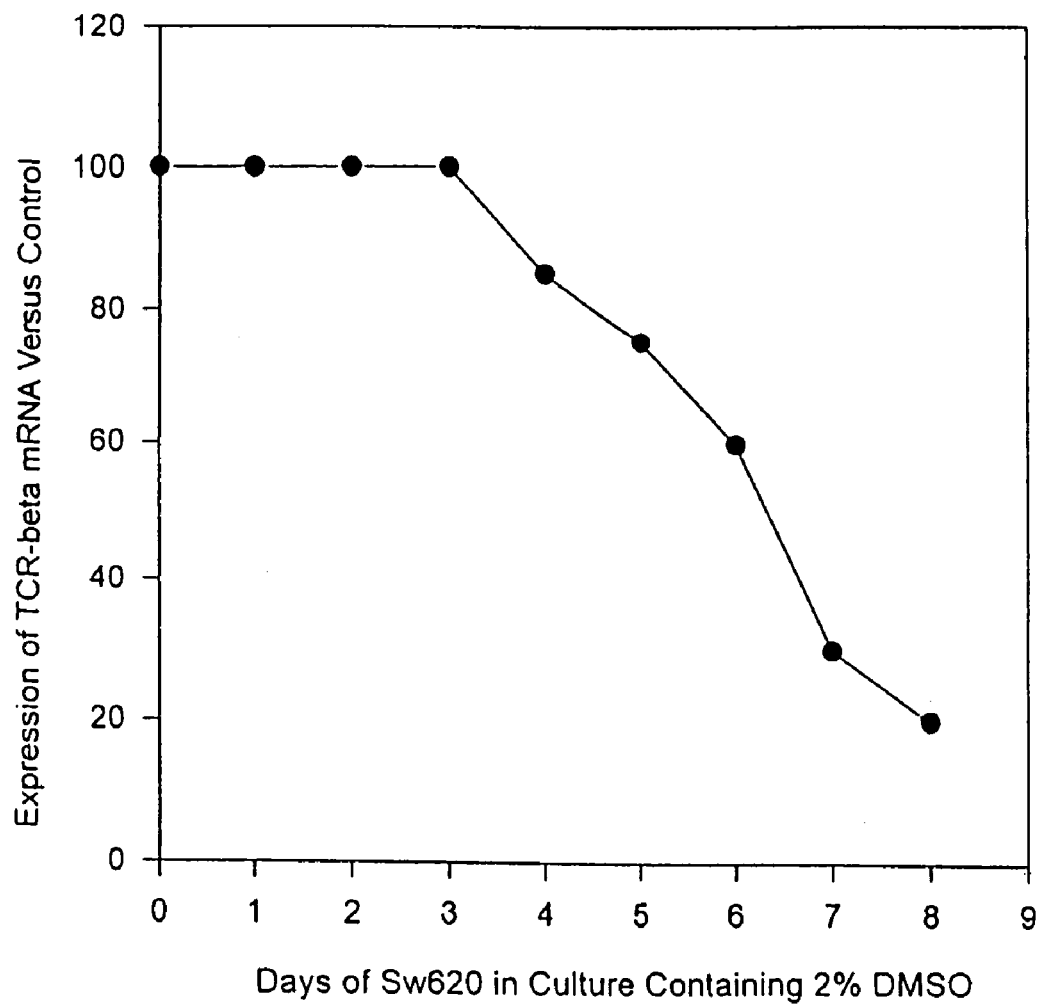
FIG. 10 is a line graph illustrating the percent of SW620 mRNA hybridizing to the 400 bp consensus sequence probe, extracted from cells exposed to culture medium containing 2% DMSO from 0 to 9 days compared to SW620 mRNA extracted from cells not exposed to DMSO over this period. Band intensities were determined using a Phosphorimager (Molecular Diagnostics, Sunnyvale Calif.) and normalized to the housekeeping gene Triose Phosphate Isomerase.

When SW620 tumor cells were incubated in 2% DMSO, there was loss of tumor-derived CD4, as discussed in Omary et al. (1991. AIDS 5:275-281). DMSO caused SW620 cells to undergo differentiation in which the morphology was changed from round (R) to epitheloid (E) and tumorigenicity was suppressed as discussed in Omary et al. (1993, *J. Cell Biochem.* 48:316-323). To determine if differentiation could alter the expression of the TCRβ message, SW620 cells were cultured with 2% DMSO for up to eight days. The cells were harvested at various times, RNA extracted and analyzed for CTβ message. As shown in FIG. 10, differentiation of the SW620 tumor cells results in a dramatic decrease in the level of the CTβ message when compared to untreated control tumor cells.

Figure 11:
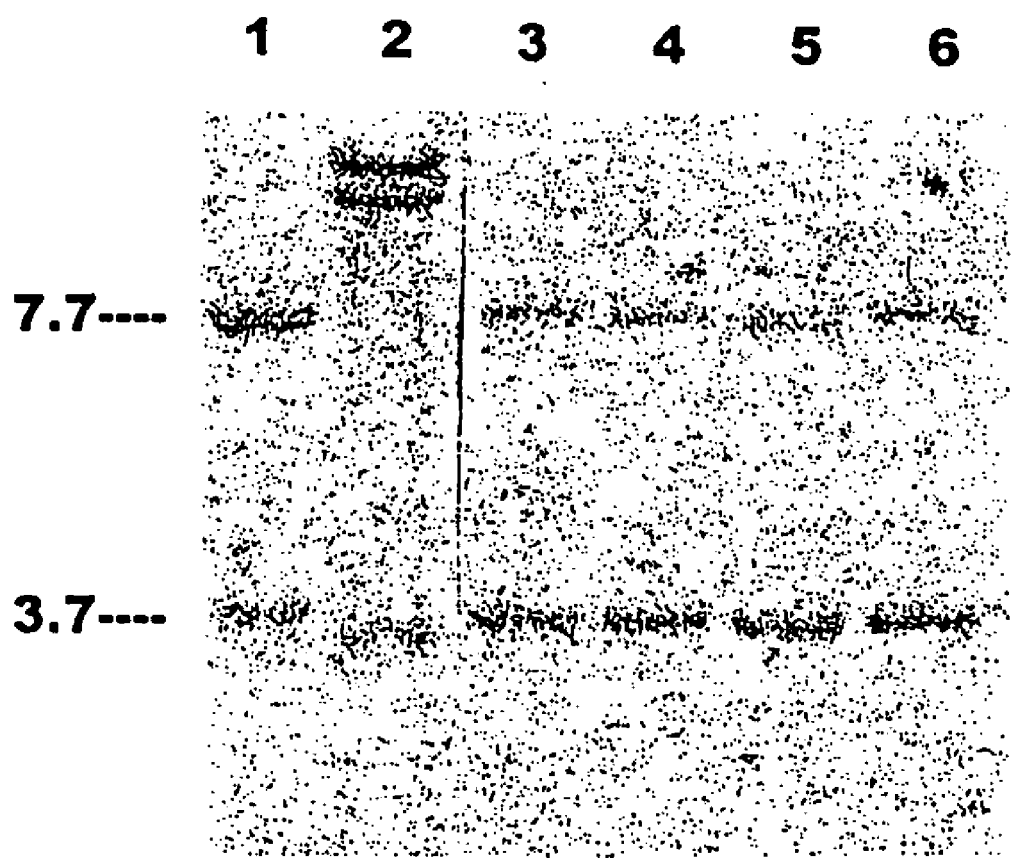
FIG. 11 is a view of determination of rearrangement of the TCRβ gene in human tumor cell lines. Southern blot analysis of genomic DNA digested with the restriction endonuclease Hind III, separated over a 0.8% agarose gel, and probed with the $^{32}$P random primer labeled consensus sequence for the constant region of the TCRβ gene (400 bpCβ probe). Each lane contained twenty μg of genomic DNA. Rearrangement disrupts the usual 7.7, 3.7 kb banding pattern seen in Hind III CTβ probed unrearranged genomic DNA. Lane 1: Raji (B cell line that does not undergo TCR rearrangement), Lane 2: control Molt-4 (T-cell Leukemia that does undergo TCR gene rearrangement), Lane 3: SW480, Lane 4: SW620, Lane 5: COLO205, Lane 6: HT-29.
Figure 12A:
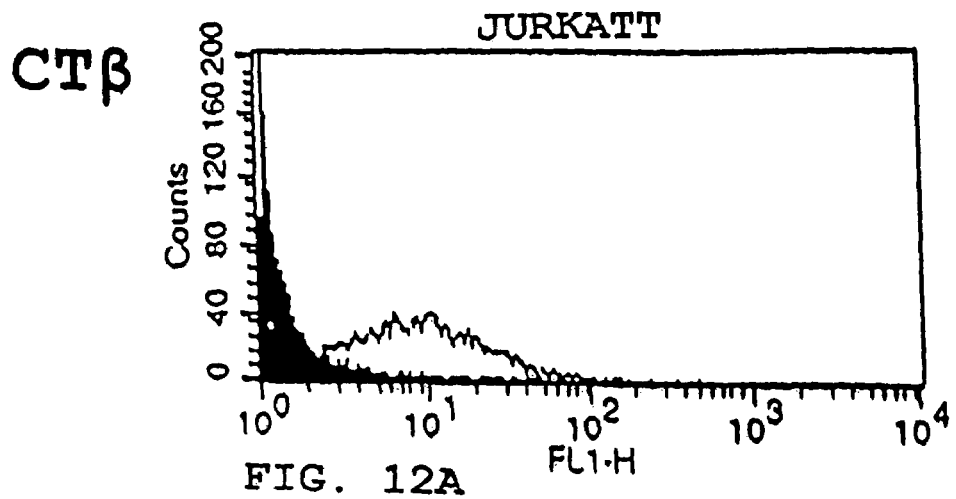
FIG. 12A is a graph using FACS analysis performed on a million cells of relative CTβ cell number (counts) versus relative fluorescence per cell (FL1-H) for the Jurkatt cell line, using FITC-labeled anti-CTβ (JOVI-1).
Figure 12B:
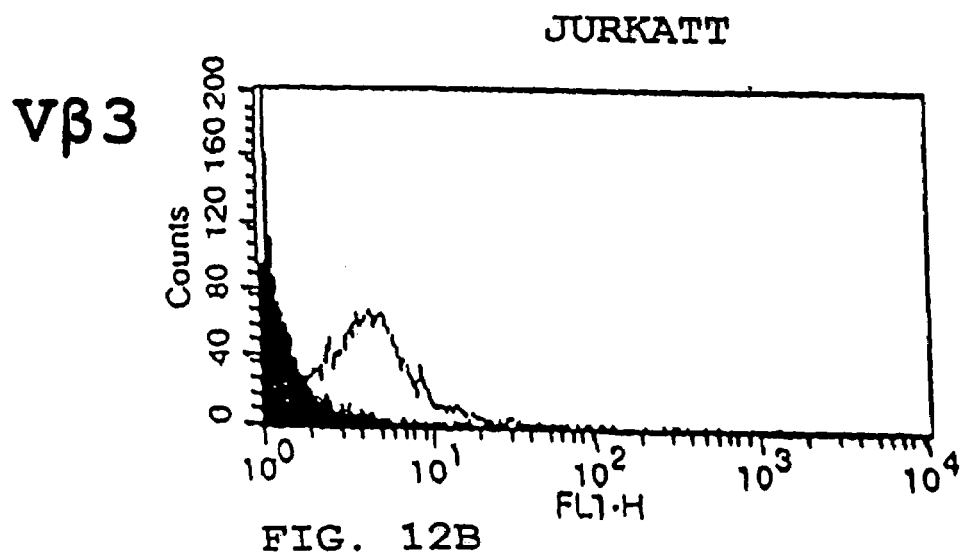
FIG. 12B is a graph using FACS analysis performed on a million cells of relative Vβ3 cell number (counts) versus relative fluorescence per cell (FL1-H) for the Jurkatt cell line, using FITC-labeled anti-Vβ3 (JOVI-3).
Figure 12C:
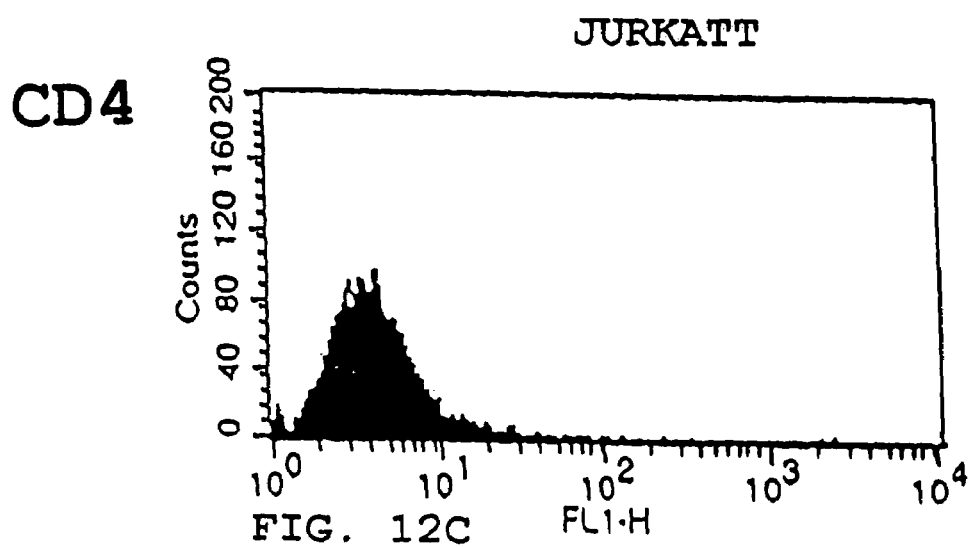
FIG. 12C is a graph using FACS analysis performed on a million cells of relative CD4 cell number (counts) versus relative fluorescence per cell (FL1-H) for the Jurkatt cell line, using FITC-labeled anti-CD4 (Q4210).
Figure 12D:
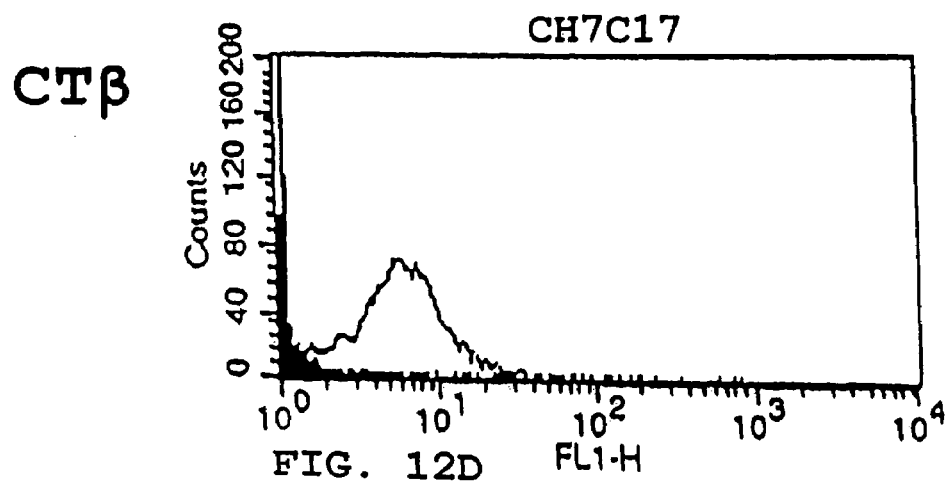
FIGS. 12D to 12F are graphs similar to those of FIGS. 12A to 12C respectively for the CH7C17 cell line.
Figure 12E:
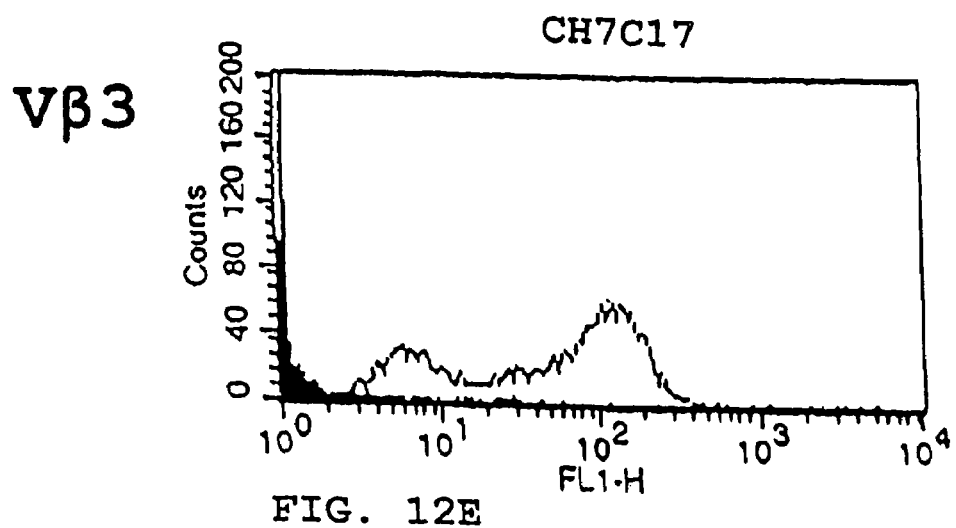
Figure 12F:
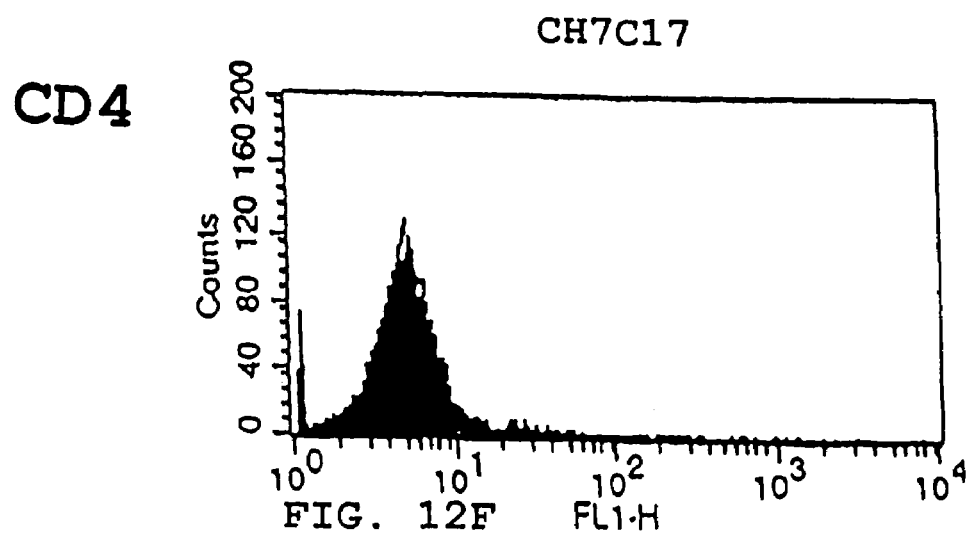
Figure 12G:
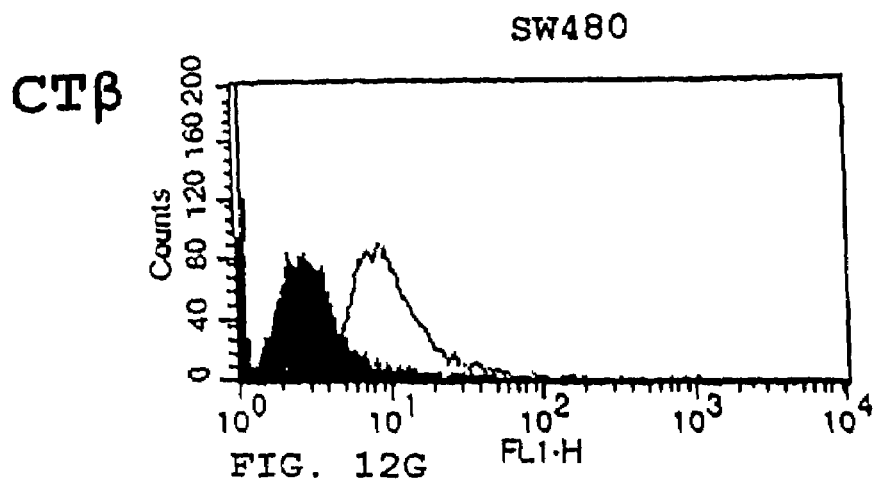
FIGS. 12G to 12I are graphs similar to those of FIGS. 12A to 12C respectively for the SW480 cell line.
Figure 12H:
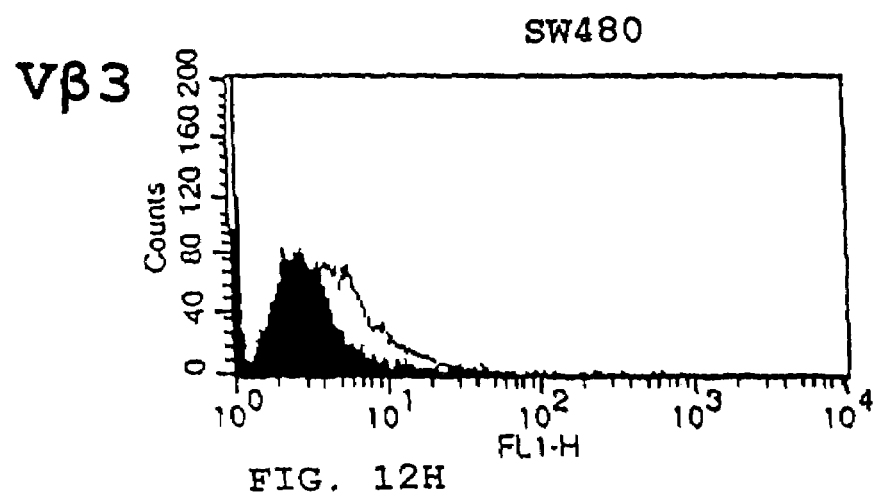
Figure 12I:
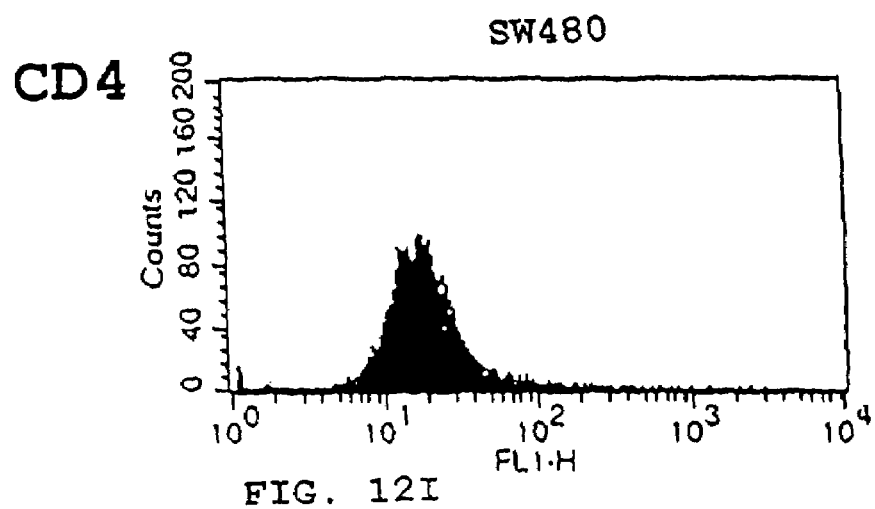
Figure 12J:
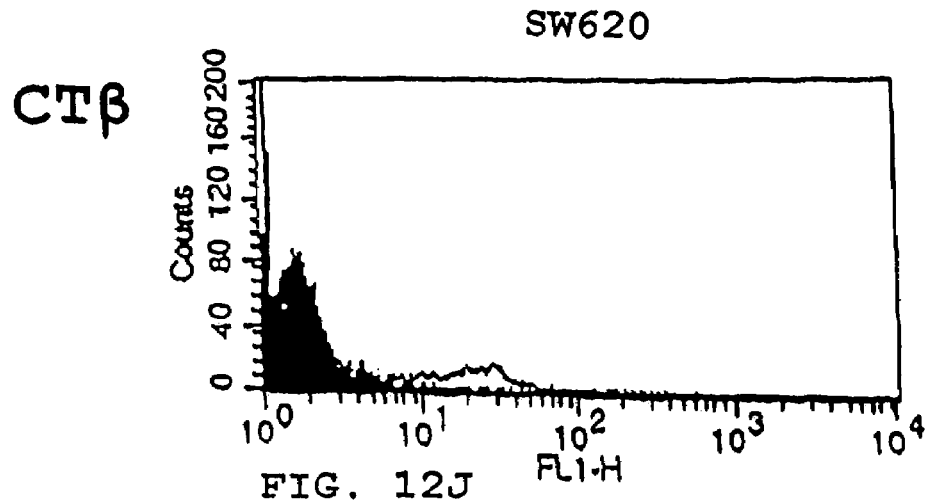
FIGS. 12J to 12L are graphs similar to those of FIGS. 12A to 12C respectively for the SW620 cell line.
Figure 12K:
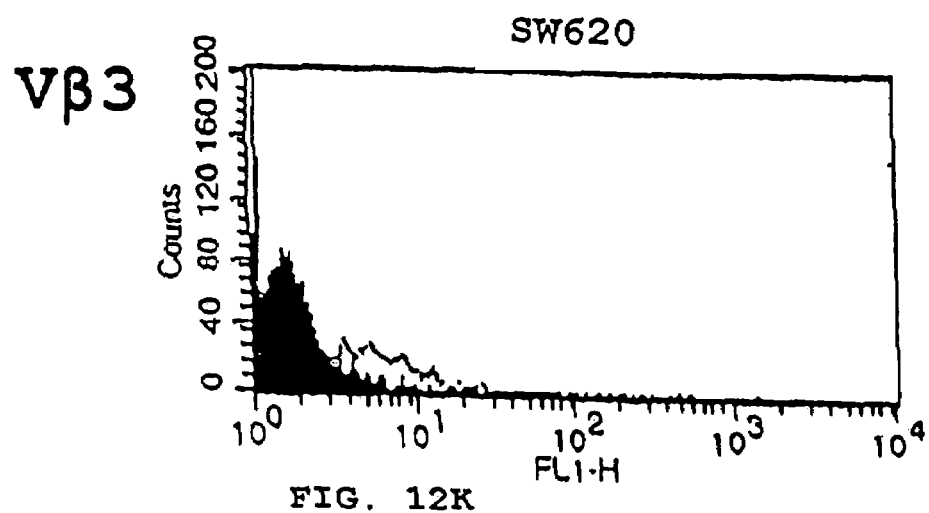
Figure 12L:
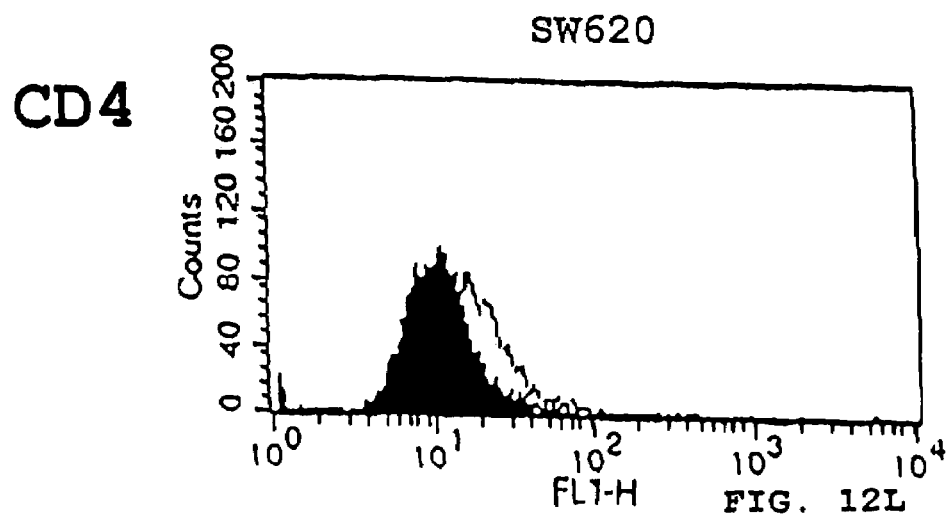

In T cell precursors, the β chain is synthesized before the α chain and then gene rearrangement occurs (Mallick et al., 1993, *Cell* 73:513-519). However, CTβ can be transcribed directly from DNA in a germline form (Candeias, S. et al. 1994, *Eur. J. Immunol.* 24:3073-3081). Therefore, a Southern blot analysis was performed to determine if rearrangement occurred in the tumor cell lines expressing the 1.0 kb CTβ transcript. FIG. 11 shows that genomic DNA from the Raji cells, SW480 tumor cells and T47D breast tumor cells do not undergo rearrangement and result in fragment sizes of 7.7 kDa, 3.7 kDa for CTβ when cut by the restriction enzymes Hind III. As control, MOLT4 cell line, a T cell derived leukemia that undergoes rearrangement, resulted in altered bands. Similar conclusions were drawn from Southern blots when DNA was cut by EcoR1 or BamH2 (data not shown).

To determine if the CTβ 1.0 kb message recognized by the cDNA probe could be translated to express a surface bound CTβ gene product, FACS analysis was carried out (FIG. 12) using FITC mouse anti-human CTβ (JOVI-1). This antibody reacts with 50-75% of T cells from control normal human peripheral blood cells (HuPBL) as shown in Viney et al. (1992, *Hybridoma* 11:701-713). SW480 and SW620 cells were surface stained for this antibody that recognizes the human CTβ1 gene product. Anti-βF1 which also recognizes the CTβ1 gene product gave the same result (not shown). However, FITC-anti-TCRα (αF1) and FITC-anti-TCRδ (δTCS1) did not stain the metastatic SW620 tumor cell line. The SW480 cell line showed a similar pattern (not shown). As a control, the T cell leukemia cell line, MOLT 4, was CTβ$^+$ while the B lymphoblast cell line RAJI was CTβ$^-$. To confirm the presence of CTβ on SW480 tumor cells and SW620 tumor cells, immunofluorescence (FIG. 13) was performed. Both of these tumor cell lines expressed surface bound CTβ.

Figure 13:
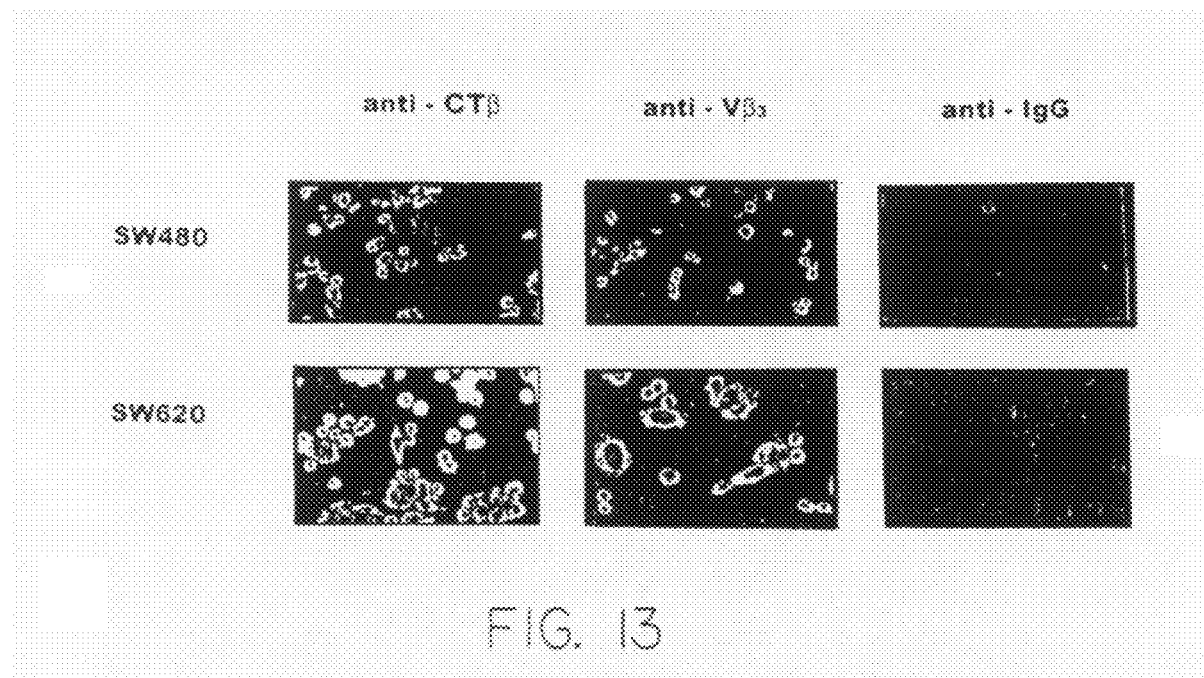
FIG. 13 is a view of determination of cell surface expression of CTβ or Vβ3 peptides by direct immuno-fluorescent staining of 0.5×10$^6$ cells with FITC-labeled anti-CTβ (JOVI-1), anti-Vβ3 (JOVI-3), or control (rabbit anti-mouse IgG).
Figure 14:
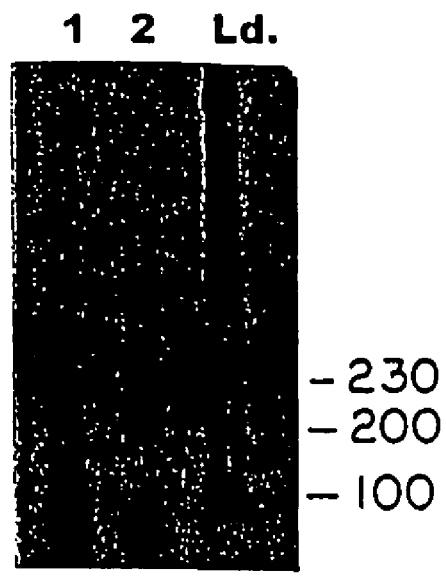
FIG. 14 is a view of PCR analysis of human peripheral blood leukocyte (HuPBL) and SW620 cDNA. Primers Vβ-3S1: sense primer in the variable region and CTβ-A1: anti-sense primer in the constant region, separated by 200-230 bp in the intact TCRβ transcript of mature T cells, were used to determine rearrangement of the 1.0 kb transcript in the colon tumor cell line SW620. The HuPBL band of roughly 230 bp indicates the presence of a normally oriented single TCR β transcript containing both Vβ3 and CTβ mRNA. Note that the lack of such a band in the SW620 lane reflects the lack of a similar single TCR β transcript in SW620 cDNA. Lane 1: SW620 cDNA, Lane 2: cDNA from human peripheral blood leukocytes, Lane Ld.: 0.1 kb ladder.
Figure 15:
FIG. 15 is a view of PCR analysis of cDNA from colon tumor cell lines using paired internal Vβ3S1 primers (Vβ3NS1 and Vβ3NAS1, 150 bp); lanes 1-4, and CTβ primers (CTβ3S1 and CTβAS1, 290 bp); lanes 5-8. The cDNA was obtained from purchased or constructed libraries with reported genomic contamination of less than 1%. The amplified products exhibited by the SW480 and SW620 cDNA's indicate presence of CTβ and V β mRNA as single transcripts. Lane Ld: 0.1 kb ladder. Lane 1 and 5: HuPBL, Lane 2 and 6: SW620, Lane 3 and 7: SW480, Lane 4 and 8: Colo 205 cell lines.

To determine if the Vβ3 found in FIG. 13 is derived from a rearranged transcript, PCR analysis of SW620 and HuPBL cDNA was completed using a Vβ3 (sense) and Ctβ (antisense) primers. As shown in FIG. 14, a 230-kb band was present suggesting a recombined Vβ3 was present in the HuPBL control cDNA library. In contrast, the recombined transcript was not present in a SW480 cDNA library when probed with the same primers. Since SW620 colon tumor cells bind the superantigen, SEB, a molecule known to interact with Vβ of the TCRβ (Dohlstein, 1991, *Eur. J. Immunol.* 21:1229-1237), we determined whether the Vβ transcript was present on these cells. SEB binds to a limited number of Vβ's including Vβ3, Vβ12, Vβ17 and Vβ20 (Scherer et al. 1993, *Ann. Rev. Cell Biol.* 9:101-28). To determine the presence of Vβ3 in solid tumor cells, we made internal primers from a Vβ3 sequence present in the cloned T cell line; PL4.4 (Accession No. L36092). These primers were used to identify rearranged and germline Vβ3 from various cDNA libraries by PCR. As shown FIG. 15, germline Vβ3 and CTβ were present in cDNA libraries made from SW480 and SW620 colon tumor cell lines. Vβ3 but not CTβ was present in the cDNA library from COLO205 cells. In contrast, the colon tumor cell line, HT-29 did not transcribe either Vβ3 or Ctβ (not shown). The PCR products, 50 and 230 kb bands were isolated and sequenced. As shown in FIG. 16A, the CTβ nucleotide sequences from the HuPBL, SW480 and SW620 cDNA libraries were 100% homologous. COLO205 and HT-29 (not shown) did not express the CTβ transcript. In addition, Vβ3 nucleotide sequences from the HuPBL, Colo205, SW480 and SW620 cDNA libraries were 99% homologous (FIG. 16B).

SW620 tumor cells can be a target for CD8 human effector cells through a superantigen dependent cellular cytotoxic mechanism (Dohlstein et al. 1991, *Eur J. Immunol.* 21:1229-1237). Since SW620 cells do not express HLA-DR, it is likely that SEB binds and forms a bridge between surface bound germline Vβ on these colon tumor cells and HLA-DR on T cells to cause lysis of the $^{51}$Cr-SW620 target cells. Recent evidence has shown that germline Vβ can be directly transcribed and expressed on the surface of thymocytes and bone marrow cells (Oneill HC. 1995. *Immunogenetics* 42:309-314; Jolly C J., 1995, *Inter. Immunol.* 7:1147-1156; Jolly C J. Oneill H C., 1997., *Immunol. Cell Biol.* 75:13-20). We, therefore, assayed for the presence of Vβ3 and CD4 molecules on the surface of these carcinoma cell lines on SW480 and SW620 cells. As shown by FACS in FIG. 12 and by immunofluorescence in FIG. 13, both SW480 and SW620 tumor cells expressed Vβ3 while only SW620 expressed CD4.

Figure 18:
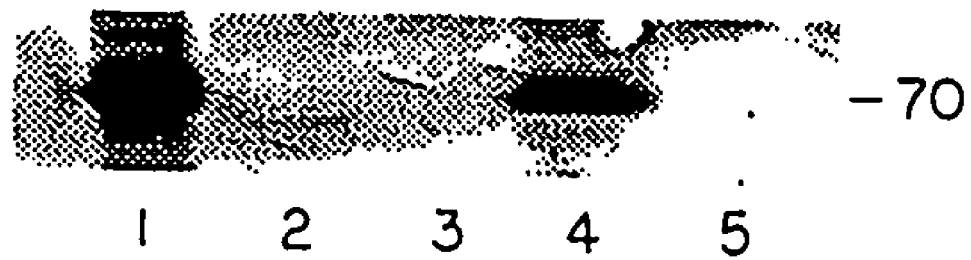
FIG. 18 is a view of a western blot of ZAP-70 (anti-human ZAP-70) from Lane 1: Jurkat; Lane 2: SW480; Lane 3: SW480E; Lane 4: SW480R and Lane 5: SW620 cell lines. ZAP-70 is 70 kDa.

Jurkat cells, SW480, SW480E, SW480R and SW620 tumor cells were cultured and lysates prepared and tested for the presence of signal transduction molecules. These molecules are found almost exclusively in T cells. The cell lysates were blotted and probed with anti-human SYK, ZAP-70, CD3R, p56$^{lck}$, and p59$^{fyn}$. The SYK family of nonreceptor protein-tyrosine kinases comprises two members; SYK and ZAP-70 (Van Oers et al. 1995, *Seminars Oncol.* 7:227-236). ZAP-70 is found exclusively in T cells and NK cells whereas SYK accumulates in most hematopoietic cells including B cells, bone marrow cells and immature T cells. As shown in FIG. 17, the 72 kDa SYK is present in Jurkat, SW480, SW480R and SW620 cells. Interestingly, SW480E cells possess both the 72 kDa immunoreactive product of SYK and a 70-kDa isoform of the protein (SYKB). It has been shown (Latour et al, 1996, *J Biol Chem* 271:22782-2290) that an isoform of SYK-B exists that is missing 23 AA in its "linker" region. Both isoforms have been shown to be present in bone marrow cells but not T cells. The function of the lower molecular weight form is unknown. In contrast, ZAP-70 (FIG. 18) was present in high amounts in SW480E cells while little or none was detected in SW480 parental cells. Further, none was observed in SW480R or SW620 cells. Why SW480E cells are the only tumor that contains ZAP-70 and both isoforms of SYK is unknown. Both SYK and ZAP-70 are crucial for hematopoietic development. The lack of ZAP-70 leads to abnormal T cell maturation while the lack of SYK reduces B cell development, hemostasis and maturation of γδ T cells. Thus ZAP-70 and SYK-B may be essential in enabling SW480E cells to be motile and invade.

Table 5 summarizes the expression of lymphoid-derived signal transduction molecules on these carcinoma cell lines. CD3ζ which is essential in coupling the TCR to ZAP-70 was present in all tumors tested. p59$^{fyn}$ was expressed on all tumor cell lines. In contrast, p56$^{lck}$ was only detected in SW480R and SW620 cells.

Figure 19:
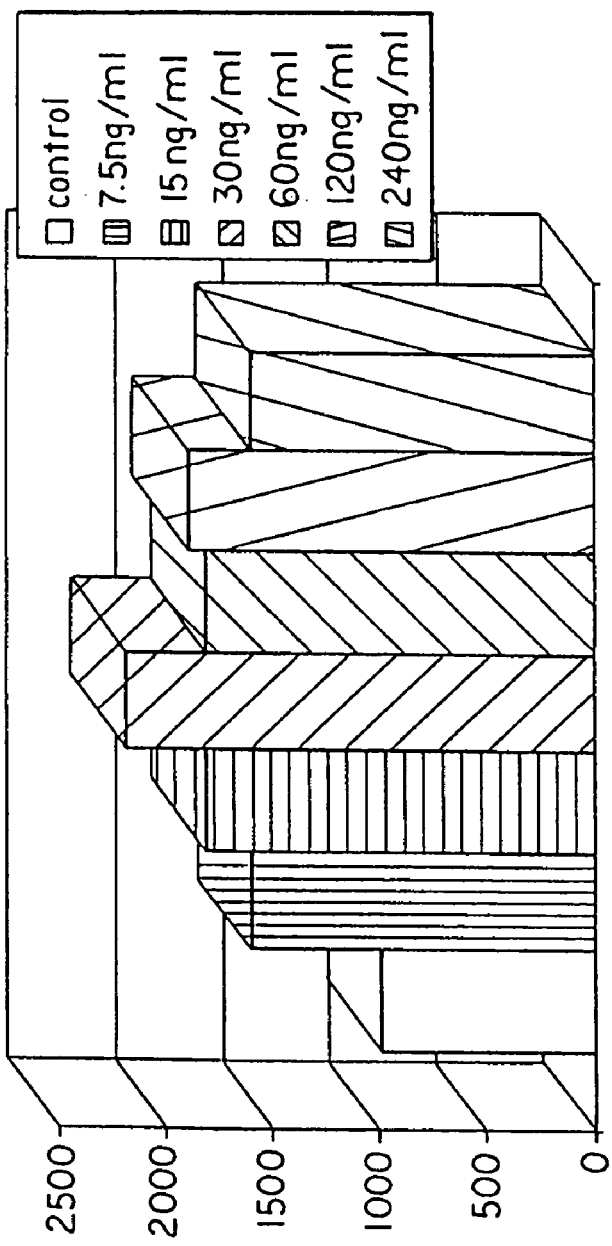
FIG. 19 is a graph showing the effect of plate bound anti-human Vβ3 on proliferation of SW620 tumor cell lines. One× 10$^4$ SW60 cells were culture with various concentrations of anti-Vβ3. Tumor cells were cultured in a 96-well plate for 72 h and pulsed with 1 μCi of 3H-Tdr for 6 h, harvested and cpm counted.
Figure 20:
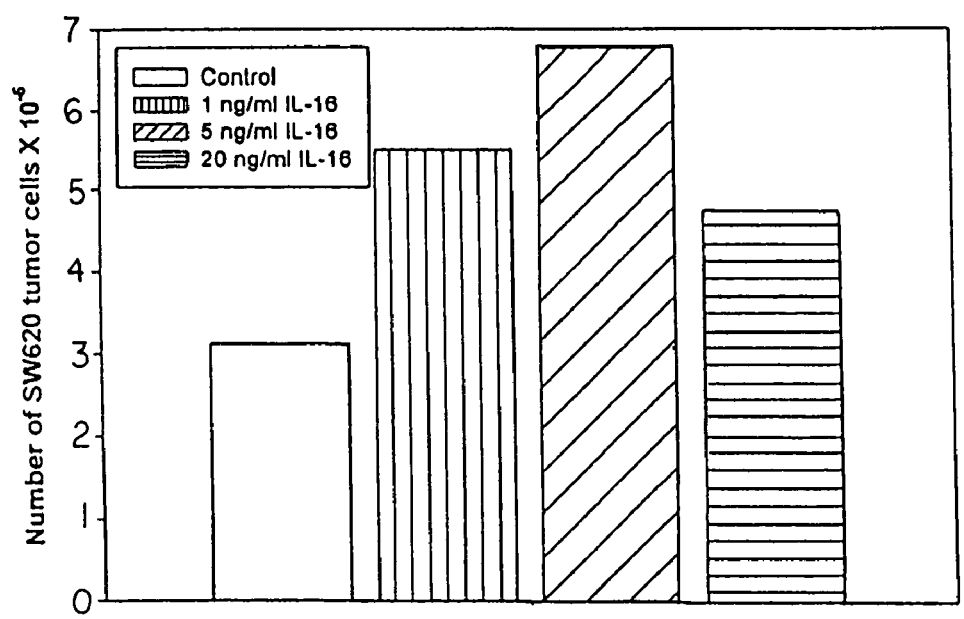
FIG. 20 is a graph showing the effect of human IL-16 on proliferation of SW620 tumor cell lines. One×10$^6$ SW620 tumor cells were culture with various concentrations of human IL-16. Tumor cells were cultured in a 24-well plates for 48 h and number of cell counted with a Coulter Counter.

Experiments were carried out to determine whether Vβ3 and CD4 on the surface of SW620 cells could be ligated with the appropriate signal. As shown in FIG. 19, plate-bound anti-Vβ3 induced SW620 tumor cells to proliferate in serum free media. Plate-bound anti-Vβ3 augmented the proliferation of (Vβ3$^+$ transfected) C7CH17 cells (Viney et al. 1992, *Hybridoma* 11:701-713). It is known that IL-16 can bind to its receptor, CD4, and ligate it (Centers et al. 1996, *Immunol. Today* 17:476-481). FIG. 20 demonstrates that the addition of IL-16 to CD4 bearing tumor SW620 cells augmented the proliferation of these tumor cells in serum free media. Thus, these two experiments indicate that tumor-derived T cell receptors are functional and therefore may be manipulated for therapy.

Figure 21:
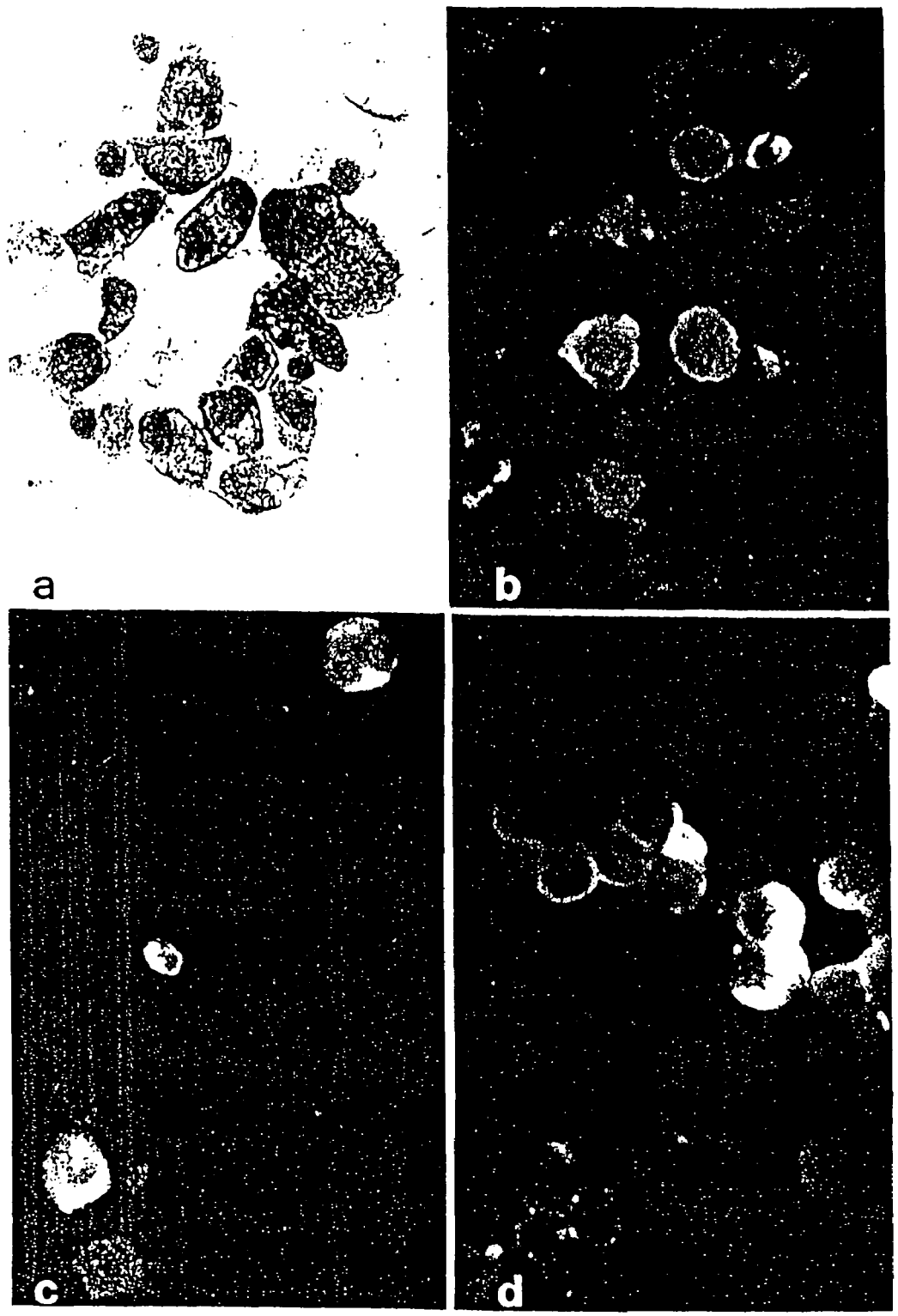
FIG. 21 is a view of immunocytochemical and fluorescence photomicrograph analysis of TdT, CD3 and βF1 on stage II and stage III human breast ductal carcinoma cells in two women. A) Tumor cell imprints made from 18 mm primary tumor of a 44-year old woman (MB/87-4906) with multiple axillary lymph node metastases (15 positive lymph nodes out of 21) show many TdT-positive cells as demonstrated by PAP procedure. These cells were also positive for CD3ε and βF1 (anti-CTβ). B) Metastatic tumor cells from an enlarged axillary lymph node of a 82-year old woman (EN/88-279) (three massive metastatic axillary lymph nodes) who had a large primary tumor (50 mm diameter) fixed to the chest wall, showed scattered TdT-positive cells as demonstrated by the indirect immunofluorescence procedure. Metastatic tumor cells from the second patient (EN/88-279) expressed C) CD3ε and D) βF1 (anti-CTβ) (×800). There was no significant difference in the number and intensity of CTβ and other T cell associated molecules between primary and metastatic tumors in these breast cancer patients.
Figure 22A:
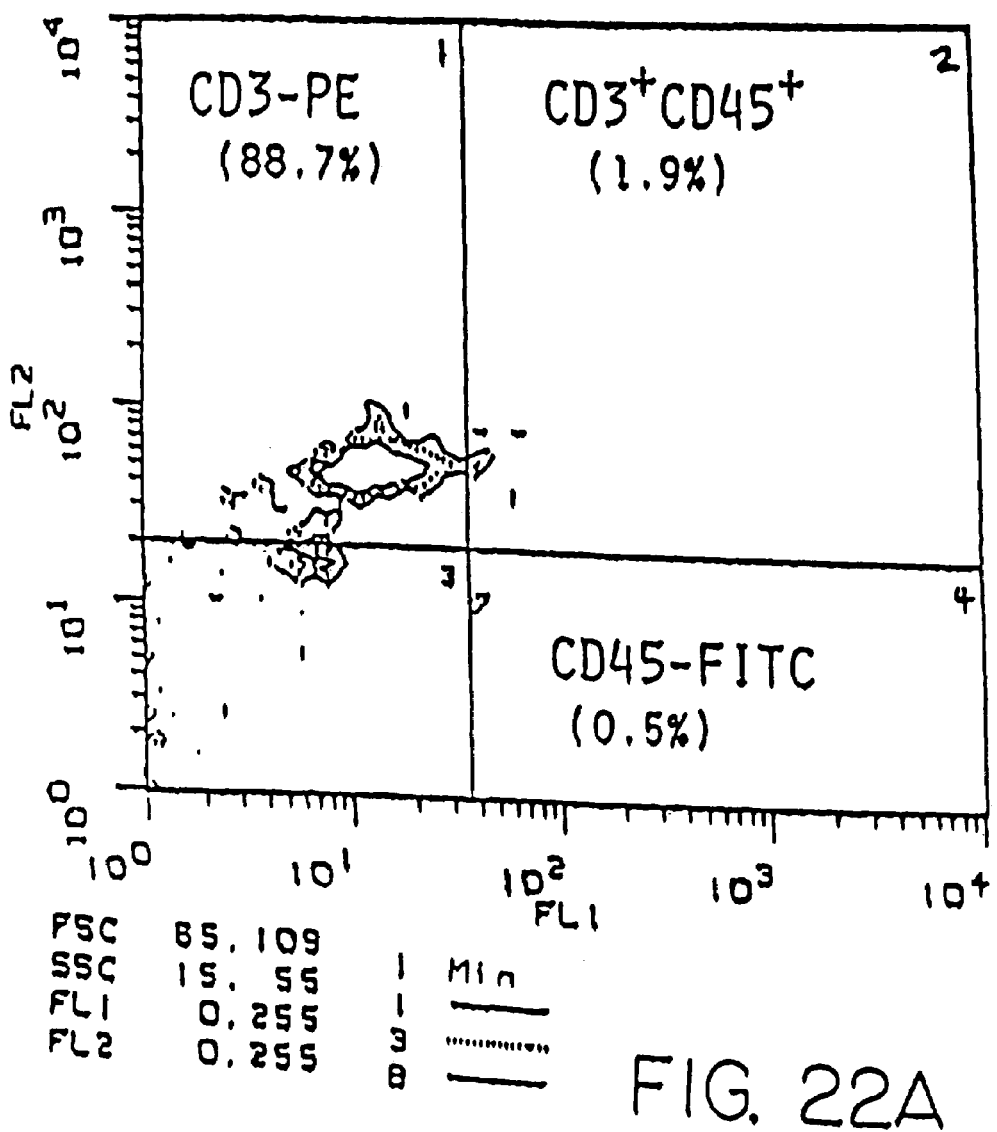
FIG. 22A is a view of FACS analysis of CD3/CD45 on Stage II breast cancer cells in a 75-year old woman.
Figure 22B:
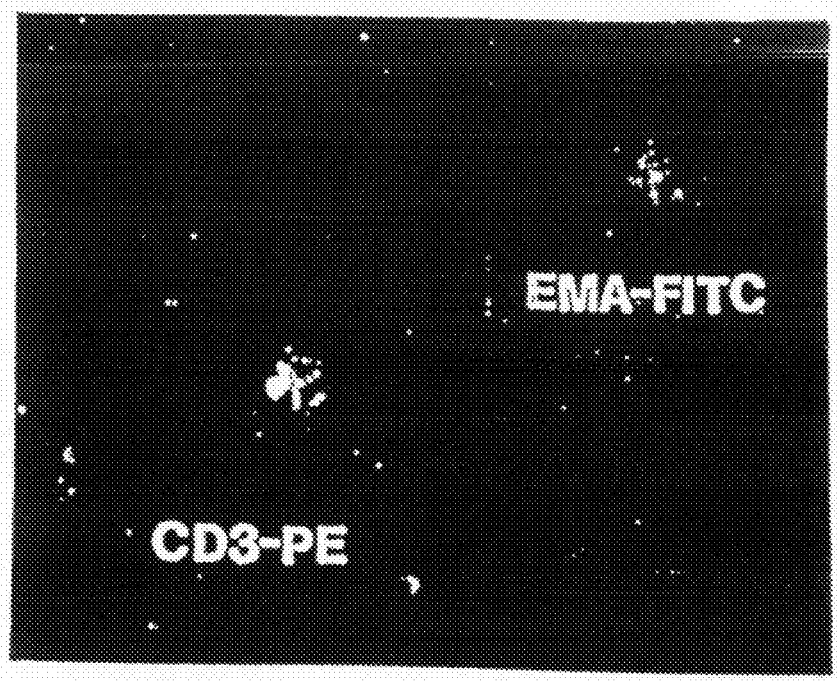
FIG. 22B is a fluorescence photomicrographic view of CD3/EMA on Stage II breast cancer cells in the 75-year old woman, PE being phytoerythrin (red dye), DITC being fluorescene isothiocyanate (green dye), and EMA being epithelial membrane antigen (indicates these cells are breast cancer cells).

The expression of lymphoid gene products was determined on biopsy samples from breast and colon cancer patients. As shown in FIG. 21A, two patients with stage II and stage III human breast ductal carcinoma cells were investigated for expression of surface T cell markers. A tumor cell imprints made from 18 mm primary tumor of a 44-year old woman (MB/87-4906) with multiple axillary lymph node metastases who had 15 positive lymph nodes out of 21 show many TdT-positive cells as demonstrated by PAP procedure. These primary tumor cells were also positive for CD3ε and βF1 (anti-CTβ) as shown in Table 6. Metastatic tumor cells from an enlarged axillary lymph node of a 82-year old woman (EN/88-279) with three massive metastatic axillary lymph nodes with a large primary tumor (50 mm diameter) fixed to the chest wall, showed scattered TdT-positive cells as demonstrated by the indirect immunofluorescence procedure (FIG. 21B). Metastatic tumor cells from this patient also expressed CD3ε (FIG. 21C) and βF1 (FIG. 21D). Table 6 also shows that the primary tumor was positive for CD3ε, CD8 and CTβ. There was no significant difference in the number or intensity of T-cell antigen-positive cells between primary and metastatic tumors in these patients. FIG. 22 shows a tumor sample from a 75-year old stage 11 breast cancer patient. 88% of this patients tumor cells were CD3 positive (FIG. 22A). These samples are also positive for epithelial membrane antigen (EMA) as shown in FIG. 22B. A further survey was carried out with 20 more breast cancer patients (Table 6). As shown in the Table, stage 1 human breast cancers that do not have regional lymph node involvement (NO) also do not express T cell associated surface molecules including βF1 (anti-CTβ), CD3ε, CD4, CD8 and TdT. In contrast, clinical samples from patients with primary breast tumors and up to three lymph nodes involved (N1-N3) expressed βF1, CD3ε, CD4, CD8 and TdT lymphocyte surface antigens. Table 7 and Table 8 contain data from additional clinical samples from breast and colon cancer patients that demonstrated the expression of Lymphoid gene products on primary and metastatic tumors.

Because of the problems that metastases present in terms of diagnosis and treatment of carcinomas, a method for determining a metastasis prognosis is desirable. One embodiment for metastasis prognosis comprises the following steps:

i) Obtain samples of the primary tumor (presurgical or intrasurgical biopsy), suspect lymph nodes, liver and serum samples;

ii) Use tissue slices or anti-epithelial antibody coupled to magnetic beads or other means to separate to obtain pure tumor cells.

iii) Obtain tumor cell suspensions and poly A mRNA from each sample.

iv) Establish the presence of lymphoid gene products in each tumor samples using PCR and the appropriate primers. These assays have the advantage of being very sensitive. The assay will measure the presence of all germline Vβ's, germline CTβ

(JOVI-1, β F1), TdT, CD3ε, CD4, CD7, CD8, CD3ζ, p59$^{fyn}$, p56$^{lck}$, ZAP-70, SYK, SKYB (70 kDa isoform) and EMA (for epithelial cells)

v.) Once established which transcripts are present, determine whether their products are present on the cell surface or intracellularly expressed (for signal transduction molecule) using FACS, immunofluorescence and western blotting. From this data, the probability of metastasis from primary tumor cells is determined.

vi) To help verify the above determinations, functional tests for tumorigenicity and metastasis may be carried out by injecting the patient's tumor cells sub-cutaneously into anti-AsGM1 (NK depleted) nude mice (or other nude animals) and, after a suitable period of time, examine the mice for local growth and lymph node and bone marrow metastasis. They may also be injected into control nude mice. Interpretation of that the tumor did not eventually metastasize. For other examples, see table 8, cases 9 to 12. The percentages of lymphoid gene products in tables 7 and 8 are the percentages of the tumor cells located in the sample. CD3, CD4, CD8, CT, and V are considered to be the more critical lymphoid gene products because they are part of the TCR receptor complex and therefore recognize antigen in context with MAC-1 and/or MAC-2. The other lymphoid gene products are considered less critical to the analysis.

The enzymatic amplification of tumor cell RNA may be used to measure the expression of message in the tumor samples. The fluorescence microscopy, FACS, Elispot and western blotting may be used to measure specific proteins in the tumor sample.

Theoretical Staging of Metastasis Based on Lymphoid Gene Products Expressed on Carcinoma Cells

| Tumor Site | Stage | Vβ | CTβ | CD4 | p56 | ZAP-70 | SYK72 | SYKB | IL-2R |
|---|---|---|---|---|---|---|---|---|---|
| Primary | | | | | | | | | |
| Noninvasive tumor cells | 1 | − | − | − | − | − | − | − | − |
| Tumor cells with invasive potential | 2 | + | + | − | − | − | + | − | − |
| Metastatic tumor cells | 3 | ++ | ++ | + | − | +++ | +++ | +++ | − |
| Secondary (distant) | | | | | | | | | |
| Tumor cells that have invaded and colonize | 4 | +++ | +++ | ++ | + | − | + | − | + | results: As previously discussed, tumorigenic/NK resistant tumor cells grow only locally in nude mice after subcutaneous injection. Metastatic/NK sensitive tumor cells are rejected by nude mice but grow locally and metastasize in anti-AsGM1 (NK depleted) nude mice. See FIGS. 7 and 8.

In order to obtain a sufficiently reliable prediction of metastatic potential, several representative samples should be obtained from different locations throughout the tumor mass since the tumor mass may not be homogeneous. The term "representative samples", as used herein and in the claims, is therefore meant to include a sufficient number of tumor sections taken from various locations including center and peripheral regions throughout the tumor mass to be assured that the prediction of metastatic potential based thereon is reliable. If no tumor cells in any of the representative samples are detected to express lymphoid gene products, then the metastatic potential of the tumor may be predicted to be low (if not zero). If a high percentage of tumor cells in any one of the representative samples are detected to express lymphoid gene products, then the metastatic potential of the tumor may be predicted to be high. While in practice grades may be assigned for various percentages of tumor cells expressing lymphoid gene products, as little as 2 to 5 percent of the tumor cells in a single representative sample expressing lymphoid gene products may be considered to be a high percentage. See, for example, case 15 in table 7 wherein 30% of the cells of SCH89-23P were EMA-positive meaning that 30% of the cells of this sample were tumor cells, and of these 6% expressed CD4 and 19% expressed CD7, yet this tumor was metastatic. The suffixes "P" and "M" in the tumor identifications in this and the other tables indicate primary and secondary (samples taken from sites to which the primary tumors had metastasized) tumors respectively. A tumor identification without such a suffix indicate a primary tumor, and either no metastasis was found or not looked for, but it couldn't be said Without being bound by theory here or elsewhere in this application, we theorize the following model of lymph node metastasis. Normal colon cells transform into preneoplastic and then neoplastic cells. These later tumor cells maintain their colonic surface properties (stage 1). However, a few of these colonic tumor cells have either i) their lymphoid genes derepressed or ii) fuse with one or more populations of hematopoietic pre-T cells to form tumor cells with invasive potential (i.e., SW480 cells, stage 2). The SW480 colon tumor cells contain two populations (SW480R and SW480E) that express lymphoid genes and their proteins. These cells are not invasive since tumorigenic SW480R cells suppress the metastatic SW480E cells. Many of the surface and signal transduction molecules in the parental SW480 population are downregulated (i.e., Vβ, CTβ, CD4, p56$^{lck}$, SYK72, SYKB, ZAP-70) compared to isolated SW480E cells. It is likely that the SW480R cells produce anti-inflammatory cytokines (IL-4, IL-10, TGFβ) that suppress various TCR and related molecules on SW480E cells. Thus, SW480E cells may not normally migrate in the presence of SW480R cells. Oreilly et al. (1996, Nature, Medicine 2:689-692) have shown that large primary tumor masses can prevent metastasis by producing substances (angiostatin) that stop the growth of new blood vessels in distant organs. The removal of the primary tumor may suppress angiostatin and allow the few remaining tumor cells to metastasize. Since metastatic cells have unstable membranes, SW480E cells may shed MHC-1. The loss of MHC-1 makes SW480E cells vulnerable to apoptosis and NK cells. IL-16 produced by endogenous CD8+ cells binds to CD4 on the SW480E cell surface, augments p56 type 1 expression and induces ZAP-70 expression resulting in metastatic tumor cells that will invade (Stage 3). The few SW480E cells that survive NK lysis may enter the lymphatic system, and travel to the lymph nodes. Metastatic SW480E cells require ZAP-70 and SYKB but not the IL-2R to migrate.

When the SW480E tumor cells are arrested in the lymph nodes, they are converted into SW620 tumor cell phenotype under endothelial control and begin to express high levels of IL-2R, TCRβ, Vβ, CD4, and p56 (Stage 4). These SW620 cells undergo clonal expansion and homeotypic aggregation when triggered by endogenous IL-2 and IL-16. The SW480E cells that remain become dormant since they do not express IL-2R or migrate without ZAP-70 expression. Thus the IL-2R is necessary for colonization but not migration. This theory suggests that the expression of lymphoid gene products on tumor cells results in a propensity for metastatic dissemination to distant sites in the same way that migrating T cells expressing the same antigens progress to their target.

In accordance with the present invention, a substance comprising a therapeutically effective amount of a molecule linked to a suitable conventional toxin, radionuclide, or chemotherapeutic agent and having binding specificity for a tumor specific lymphoid gene product idiotype is systemically administered. This molecule may, for example, be an anti-ZAP-70 or anti-SYK-B antibody or a cell permeable ZAP-70 antagonist, as discussed hereinafter.

Ligation of the Vβ chain of TCRβ and CD4 to the nonpolymorphic regions of MHC-II colocalizes Vβ and CD4. CD4 is also directly associated with the T cell signaling molecule, p56 type 1 (thymus-derived). This colocalization activates tyrosine kinases (p56) and causes a rapid cascade of intercellular signaling events. The activation of the tyrosine kinases (p56, SYK, ZAP-70) leads to phosphorylation of CD3ζ. ZAP-70 is necessary for the phosphorylation of signaling enzymes such as inositol phospholipid hydrolysis, increases in intercellular $Ca^{++}$, PKC and ultimately regulate transcriptional factors for DNA binding and gene activation or suppression. We also believe that ZAP-70 is intimately involved in tumor cell migration since it is only present in the metastatic SW480E cells. Therefore, in order to treat a solid nonlymphoid tumor, in accordance with the present invention, ZAP-70 is blocked to inhibit its phosphorylation or kinase activity and thereby inhibit metastasis by use of a cell permeable nonpeptide ZAP-70 antagonist such as, for example, a compound developed by Novartis Pharma Ltd of Switzerland and described in Revesz et al, 1997, *Bioorganic and Med Chem Letters.* 7:2875-2878, and by other means.

The tables referred to herein are appended hereto.

Although the invention has been described in detail herein, it should be understood that the invention can be embodied otherwise without departing from the principles thereof, and such other embodiments are meant to come within the scope of the present invention as defined by the appended claims.

TABLE 1

Ability of Nonmetastatic (NM081) Rat Mammary Tumor Cells to Fuse with Thymocytes or Macrophages and Converted into Lymph Node (NM-T2) or Lung (NM-M2) Derived Metastatic Cells[1]

| Cells | Differentiation State | Metastasis Site | CD3 | CD8 | Mac-1 |
|---|---|---|---|---|---|
| NM081 tumor cells | +++ | − | − | − | − |
| NM-T2 (NM081 + thymocytes) | + | Lymph Node | + | + | − |
| NM-M2 (NM081 + macrophages) | + | Lung | − | − | + |
| thymocytes | − | − | + | + | − |
| macrophages | − | − | − | − | + |

[1]Nonmetastatic NM081 rat mammary tumor cells were fused with thymocytes or peritoneal macrophages by standard methods and the hybrid tumor cells phenotyped for CD3, CD8, or Mac-1 or injected sub-cutaneously into syngeneic rats and metastasis determined.

Note: the greater the number of +s is correlated to the degree of the respective property, and a − indicates that the respective property is not present or is negative.

TABLE 2

Expression of Lymphoid Markers on Murine Nonlymphoid Tumor Cells

| | | Melanoma | Colon Carcinoma | | | | Mammary Carcinoma | |
|---|---|---|---|---|---|---|---|---|
| Marker | Met–> | B16F10 H | MCA-26 H | MCA-38 H | 51B L | 51B110 H | MC4908 L | MC7849 H |
| Vβ8 | | ++ | ++ | ++ | ND | ND | ND | ND |
| TCRαβ | | ++ | ++ | ++ | + | ++ | + | ++ |
| TCRγδ | | − | − | − | − | − | − | − |
| Thy1.2 | | +++ | +++ | +++ | ND | ND | +++ | ND |
| CD3ε | | ± | ± | ± | − | ± | − | ± |
| CD4 | | + | + | + | + | + | + | + |
| CD5 | | ND | ++ | ND | ND | ND | ND | ND |
| CD8 | | − | − | − | − | − | − | − |
| CD44 | | ++ | ++ | ++ | ++ | ++ | ++ | ++ |
| IL-2Rα | | +++ | +++ | +++ | ND | ND | + | +++ |
| NK1.1 | | − | − | − | − | − | ND | ND |
| MAC-1 | | ND | − | ND | ND | ND | ND | ND |

Met = Metastatic potential; [H] high; [L] low

Direct immunofluorescence staining: [+++] highly positive cells; [++] mostly positive cells; [+] some positive cells; [−] negative cells; [ND] not done

TABLE 3

Properties of Breast Cancer Cell Lines Derived from Wistar Furth Rats

| Tumor | differentiation state | estrogen receptor | CD4 | CD8 | metastatic site |
|---|---|---|---|---|---|
| A. Nonmetastasizing | | | | | |
| MT-W9 | ++ | + | − | − | − |
| MTW9A | +++ | ++ | − | − | − |
| MTW9B | + | + | − | − | − |
| MTW9C | + | − | − | − | − |
| MTW9D | + | − | − | − | − |
| Lymphogenous and hematogenous metastasizing | | | | | |
| MT449 | ++ | − | + | − | LN, lung |
| MT450 | +++ | + | + | − | LN, lung, liver, brain |
| B. Nonmetastasizing | | | | | |
| MT-100 | + | ND | − | − | − |
| Lymphogenous metastasizing | | | | | |
| SMT-2A | + | ND | − | + | LN, bone |
| Lymphogenous and hematogenous metastasizing | | | | | |
| TMT-081 | + | ND | + | − | LN, lung, spleen |

Note: the greater the number of +30s is correlated to the degree of the respective property, and a indicates that the respective property is not present or is negative.

TABLE 4

Tumorigenicity and Metastatic Potential of Human Colon Tumor Cell Lines[1]

| Property | SW480 | SW480E | SW480R | SW620 |
|---|---|---|---|---|
| Morphology | E + R | E | R | R |
| Dominance in cell fusion | − | + | | |
| Adhesiveness | | Good | Poor | |
| Growth characteristics | | Monolayer | Pile-up | |
| Doubling time | | 32 h | 15 h | |
| NK sensitivity | | +++ | − | |
| MHC-1 expression | + | + | +++ | +++ |
| Motility in vitro | | +++ | − | |
| Tumorgenicity in vivo (SC: local growth in nude) | | − | ++++ | |
| Lymph node metastasis (SC:LN mets in non NK depleted nude) | | − | − | |
| Lymph Node metastasis (SC:LN mets in NK depleted nude) | | +++ | − | |
| Immunogenic | | − | + | |
| Shedding of TAA | | + | − | |

E = epitheloid
R = round
Note: the greater the number of +s is correlated to the degree of the respective property, and a − indicates that the respective property is not present or is negative.

TABLE 5

Expression of T Cell Derived Signal Transduction Molecules in Colon Tumor Cell Lines[1]

| Property | Jurkat | SW480 | SW480E | SW480R | SW620 |
|---|---|---|---|---|---|
| CD3ζ | + | + | + | + | |
| p56 type 1 | + | − | | ++ | ++ |
| p59 | + | + | + | + | + |
| ZAP-70 | + | + | +++++ | − | − |
| SYK72 | + | + | ++ | + | + |
| SYK70 | − | − | ++ | − | |

[1]Determined by western blotting
Note: the greater the number of +s is correlated to the degree of staining, and a ± denotes borderline staining, and a indicates no staining.

TABLE 6

T-cell Associate Molecules in Fresh Human Breast Cancer Cells by Immunocytochemistry

| Patient I.D. code | Age status | TNM | TdT | CD3 | CTβ | CD8 | CD4 |
|---|---|---|---|---|---|---|---|
| Stage I | | | | | | | |
| LD/88-730 | 32 | T1N0 | − | | − | − | − |
| MA/DMH-1349 | 38 | T1N0 | | | − | − | − |
| JF/87-5056 | 45 | T2N0 | − | | | − | − |
| NP/87-8803 | 49 | T1N0 | | | − | − | − |
| SM/87-7843 | 50 | T1N0 | − | | | − | − |
| TG/88-I506 | 56 | T1N0 | − | | | − | − |
| BK/88-1791 | 56 | T1N0 | | | − | − | − |
| JS/SCH-3483 | 62 | T2N0 | | | | + | ± |
| IN/88-997 | 62 | T1N0 | − | | | − | − |
| IA/88-1677 | 63 | T1N0 | | | | − | − |
| D0/87-5124 | 69 | T1N0 | ± | | | − | − |
| IT/88-734 | 73 | T2N0 | ++ | | | − | − |
| AD/88-2004 | 79 | T1N0 | | | | − | − |
| Stage II and III | | | | | | | |
| KS/88-1526 | 34 | T1N2 | | ++ | +++ | ++ | + |
| MB/87-4906[1] | 44 | T2N2 | +++ | + | ++ | | |
| SW/88-2794 | 44 | T2N1 | + | + | + | + | ++ |
| LJ/88-1010 | 52 | T3N3 | +++ | + | | | |
| BR/87-4991 | 55 | T2N1 | ++ | ± | ± | ± | ± |
| LC/88-2055 | 57 | T2N1 | | ++ | ++ | + | ++ |
| EN/88-279[2] | 82 | T1N2 | ++ | ++ | ++ | ++ | |

T1 = stage 1; T2 = stage 2; T3 = stage 3
N = 0; no lymph node involvement
N = 1; 1 lymph node involved
N = 2; 2 lymph nodes involved
Ctβ is βF1 (T cell Sciences) and is directed to CTβ chain of human TCR
TdT is Terminal Deoxynucleotidyl Transferase
[1]see FIG. 21see FIG. 21
The greater the number of +s is correlated to the degree of staining, a ± denotes borderline staining, and a − indicates no staining.

TABLE 7

Flow Cytometric Analysis Of Fresh Human Breast Cancer Cells for the Expression of T-cell Associated Molecules

| Case No. | CD3 | CD4 | CD8 | CD14 | CD45 | CD7 | Leu-8 | EMA |
|---|---|---|---|---|---|---|---|---|
| 1. S89-5825 | 1% | | 1% | 5% | 1% | | | |
| 2. S89-5827 | 2 | 1 | 2 | | 3 | | | |
| 3. S89-5938P | | 89 | 2 | 1 | 1 | 2 | | |
| S89-5938M | 5 | 2 | 1 | | 5 | | | |
| 4. S89-6280 | 1 | 1 | 1 | 2 | 10 | | | |
| 5. 589-6296M | | 55 | 43 | 29 | 13 | 28 | | |
| 6. S89-6508 | | 6 | 5 | 20 | | 36 | | |
| 7. S89-6756P | | 25 | 16 | 11 | 10 | 42 | 32 | |
| S89-6756M | | 12 | 0 | 0 | 2 | 55 | 12 | |
| 8. S89-6923 | | 71 | | | | 42 | 51 | |
| 9. S89-7153 | | 7 | 3 | 3 | 5 | 9 | 3 | 51 |
| 10. S89-7239 | 14 | | | 2 | 29 | | | 21 |

TABLE 7-continued

Flow Cytometric Analysis Of Fresh Human Breast Cancer Cells for the Expression of T-cell Associated Molecules

| Case No. | CD3 | CD4 | CD8 | CD14 | CD45 | CD7 | Leu-8 | EMA |
|---|---|---|---|---|---|---|---|---|
| 11. S89-7396 | 71 | 60 | 4 | 54 | 54 | | | 52 |
| 12. DM89-4435 | | 10 | 6 | 1 | 2 | 11 | | 56 |
| 13. DM89-4462 | | 11 | 8 | 5 | 4 | 17 | | 46 |
| 14. SCH22-M | | 49 | 15 | 6 | | 24 | | |
| 15. SCH89-23P | | 6 | 1 | 0 | 0 | 19 | 11 | 30 |
| SCH89-23M | 19 | 9 | 5 | | 39 | 10 | | 20 |
| 16. S90-686M | | 14 | 0 | | 2 | 23 | | |

FACScan histograms on this analysis and direct immunocytochemistry of unsorted cell smear.

TABLE 8

Flow Cytometric Analysis of Human Colorectal Cancer Cells for the Expression of T-cell Associated Molecules

| Case No. | T cell markers | | | | | | | CEA |
|---|---|---|---|---|---|---|---|---|
| | CD3 | CD4 | CD8 | CD14 | CD45 | CD7 | Leu-8 | |
| 1. S89-5919 | 10% | 4 | 9 | 3 | 20 | | | |
| 2. S89-5971 | 36 | 10 | 4 | | 4 | | | |
| 3. S89-6499 | 22 | 1 | 1 | 10 | 42 | | | |
| 4. S89-6657 | 10 | 4 | 4 | | 18 | | | |
| 5. S89-6671 | 2 | 1 | 7 | 15 | 15 | 10 | | |
| 6. DM89-3931 | 2 | 3 | 3 | | | 10 | | |
| 7. DM89-4337 | 15 | 8 | 2 | 2 | 27 | 11 | 53 | |
| 8. S89-7418 | 7 | 1 | 1 | 2 | 12 | | 73 | |
| 9. S89-7438P | 4 | 2 | 1 | 2 | 7 | 3 | 46 | |
| S89-7438M | 27 | 21 | 1 | 1 | 44 | 5 | 50 | |
| 10. S89-7616M | 24 | 17 | 8 | 6 | 36 | 18 | 25 | |
| 11. DM89-4554 | 6 | 3 | 2 | 8 | 20 | 3 | 58 | |
| 12. S590-329P | 7 | | 5 | | 2 | 40 | | |
| S590-329M | 3 | 3 | 2 | 2 | 3 | 1 | 2 | 88 |
| 13. S90-580M | 4 | 2 | 1 | 1 | 3 | 2 | 45 | |

FACScan histograms on this analysis and direct immunocytochemistry of unsorted cell smear.

---

What is claimed is:

1. A method of predicting lymphotrophic metastatic potential of a primary human colon tumor, the method comprising obtaining a plurality of samples from said primary tumor and determining the expression of SYKB, wherein expression of SYKB in any of the plurality of samples is indicative that the primary colon tumor has lymphotrophic metastatic potential.

* * * * *

SEQUENCE LISTING

<160> NUMBER OF SEQ ID NOS: 7

<210> SEQ ID NO 1
<211> LENGTH: 269
<212> TYPE: DNA
<213> ORGANISM: Homo sapiens

<400> SEQUENCE: 1

```
tgcacagtgg ggtcagcaca gacccgcagc ccctcaagga gcagcccgcc ctcaatgact        60
ccagatactg cctgagcagc cgcctgaggg tctcggccac cttctggcag aaccccccgca      120 accacttccg ctgtcaagtc cagttctacg ggctctcgga gaatgacgag tggacccagg      180
atagggccaa acccgtcacc cagatcgtca gcgccgaggc ctggggtaga gcagactgtg      240
gctttacctc ggtgtcctac cagcaaggg                                        269
```

<210> SEQ ID NO 2
<211> LENGTH: 269
<212> TYPE: DNA
<213> ORGANISM: Homo sapiens

<400> SEQUENCE: 2

```
tgcacagtgg ggtcagcaca gacccgcagc ccctcaagga gcagcccgcc ctcaatgact        60
ccagatactg cctgagcagc cgcctgaggg tctcggccac cttctggcag aaccccccgca      120 accacttccg ctgtcaagtc cagttctacg ggctctcgga gaatgacgag tggacccagg      180
atagggccaa acccgtcacc cagatcgtca gcgccgaggc ctggggtaga gcagactgtg      240
gctttacctc ggtgtcctac cagcaaggg                                        269
```

<210> SEQ ID NO 3
<211> LENGTH: 269
<212> TYPE: DNA
<213> ORGANISM: Homo sapiens

```
<400> SEQUENCE: 3
tgcacagtgg ggtcagcaca gacccgcagc ccctcaagga gcagcccgcc ctcaatgact      60
ccagatactg cctgagcagc cgcctgaggg tctcggccac cttctggcag aaccccccgca    120 accacttccg ctgtcaagtc cagttctacg ggctctcgga gaatgacgag tggacccagg    180 ataggccaa acccgtcacc cagatcgtca gcgccgaggc ctggggtaga gcagactgtg     240
gctttacctc ggtgtcctac cagcaaggg                                      269

<210> SEQ ID NO 4
<211> LENGTH: 113
<212> TYPE: DNA
<213> ORGANISM: Homo sapiens

<400> SEQUENCE: 4
tggggctacg gctgatctat ttctcatatg atgttaaaat gaaagaaaaa ggagatattc     60
ctgaggggta cagtgtctct agagagaaga aggagcgctt ctccctgatt ctg           113

<210> SEQ ID NO 5
<211> LENGTH: 113
<212> TYPE: DNA
<213> ORGANISM: Homo sapiens

<400> SEQUENCE: 5
tgcggctacg gctgatctat ttctcatatg atgttaaaat gatagaaaaa ggagatatcc     60
ctgaggggta cagtgtctct agagagaaga aggagtgctt ctccctgatt ctg           113

<210> SEQ ID NO 6
<211> LENGTH: 113
<212> TYPE: DNA
<213> ORGANISM: Homo sapiens

<400> SEQUENCE: 6
tgcggctacg gctgatctat ttctcatatg atgttaaaat gatagaaaaa ggagatatcc     60
ctgaggggta cagtgtctct agagagaaga aggagtgctt ctccctgatt ctg           113

<210> SEQ ID NO 7
<211> LENGTH: 113
<212> TYPE: DNA
<213> ORGANISM: Homo sapiens

<400> SEQUENCE: 7
tgcggctacg gctgatctat ttctcatatg atgttaaaat gaaagaaaaa ggagatatcc     60
ctgaggggta cagtgtctct agagagaaga aggagtgctt ctccctgatt ctg           113
```